United States Patent [19]
Sakai et al.

[11] Patent Number: 5,901,071
[45] Date of Patent: May 4, 1999

[54] METHOD OF EVALUATING CORROSION RESISTANCE OF METAL MATERIAL, METHOD OF DESIGNING ALLOY OF HIGH CORROSION RESISTANCE, METHOD OF DIAGNOSING CORRODED STATE OF METAL MATERIAL, AND METHOD OF OPERATING PLANT

[75] Inventors: Masanori Sakai, Hitachiota; Noriyuki Ohnaka, Hitachinaka; Yuichi Ishikawa, Mito; Haruo Fujimori, Hitachiota; Yusuke Isobe; Takuya Takahashi, both of Hitachi, all of Japan

[73] Assignee: Hitachi, Ltd., Tokyo, Japan

[21] Appl. No.: 08/496,586

[22] Filed: Jun. 28, 1995

[30] Foreign Application Priority Data

Jul. 8, 1994 [JP] Japan .................................. 6-157567

[51] Int. Cl.⁶ .................................................. G06F 17/00
[52] U.S. Cl. ................................ 364/578; 148/240; 436/6
[58] Field of Search .............................. 364/469.02, 578, 364/512; 436/6; 148/240, 287

[56] References Cited

U.S. PATENT DOCUMENTS

| 5,369,370 | 11/1994 | Stratmann et al. ...................... 324/663 |
| 5,519,330 | 5/1996 | Yamauchi et al. ....................... 324/700 |
| 5,569,334 | 10/1996 | Kawata et al. ........................... 148/287 |
| 5,580,398 | 12/1996 | Ohmi ...................................... 148/280 |

FOREIGN PATENT DOCUMENTS

| 0 358 994 | 3/1990 | European Pat. Off. ......... G21C 17/00 |
| 0 450 440 A1 | 10/1991 | European Pat. Off. ....... G21C 13/087 |
| 0 515 112 A1 | 11/1992 | European Pat. Off. ......... C22C 38/40 |
| 6-058903 | 4/1994 | Japan .............................. G01N 27/26 |
| WO 91/19972 | 12/1991 | WIPO ............................. G01N 27/00 |

OTHER PUBLICATIONS

Oriani, R.A., "Consequence of Strain Induced Electric Field at Roots of Cracks," Metallurgica, vol. 5:697–700 (1971).

Gorse, et. al., "The Effect of Ageing on Passive Films Formed on Stainless Steels by Annealing in Hydrogen Atmospheres," Pd. og–1992, pp. 1455–1470.

Vetter, K.J., "General Kinetics of Passive Layers on Metals," Electrochimica Acta, vol. 16:1923–1937 (1971).

Kloppers, M.J. et al., Electronic Properties and Defect Structure of Fe and Fe–Cr Passive Films, Corrosion—vol. 48, No. 3, pp. 229–238.

*Primary Examiner*—Kevin J. Teska
*Assistant Examiner*—A. S. Roberts
*Attorney, Agent, or Firm*—Pennie & Edmonds LLP

[57] ABSTRACT

The composition of an alloy is inhomogeneous, so that the Fermi level of electrons in the surface of the alloy differs depending upon positions. It is accordingly considered that a part susceptible to corrosion and a part less susceptible thereto will coexist in the alloy. The corrosion rate of the alloy is indicated as the exponential function of a potential difference ($\Delta\Phi_H$) within an electric double layer. The potential difference remains unchanged as long as the Fermi level lies within the forbidden band of the electrons. However, in a range in which the Fermi level falls within the valence band of the electrons, the lowering thereof leads to the increase of the potential difference. Accordingly, a corrosion-resisting alloy is designed in accordance with the following guidelines: a) The electron energy level (Ev) of the valence band is low, b) an oxide film to be formed on the alloy is an n-type semiconductor, c) a band gap (Ec-Ev) is wide where Ec denotes the conduction band of the electrons, and d) a flatband potential ($E_{fb}$) is low. Further, the operation of a plant and the evaluation of a corrosional damage can be based on such a theory.

4 Claims, 24 Drawing Sheets

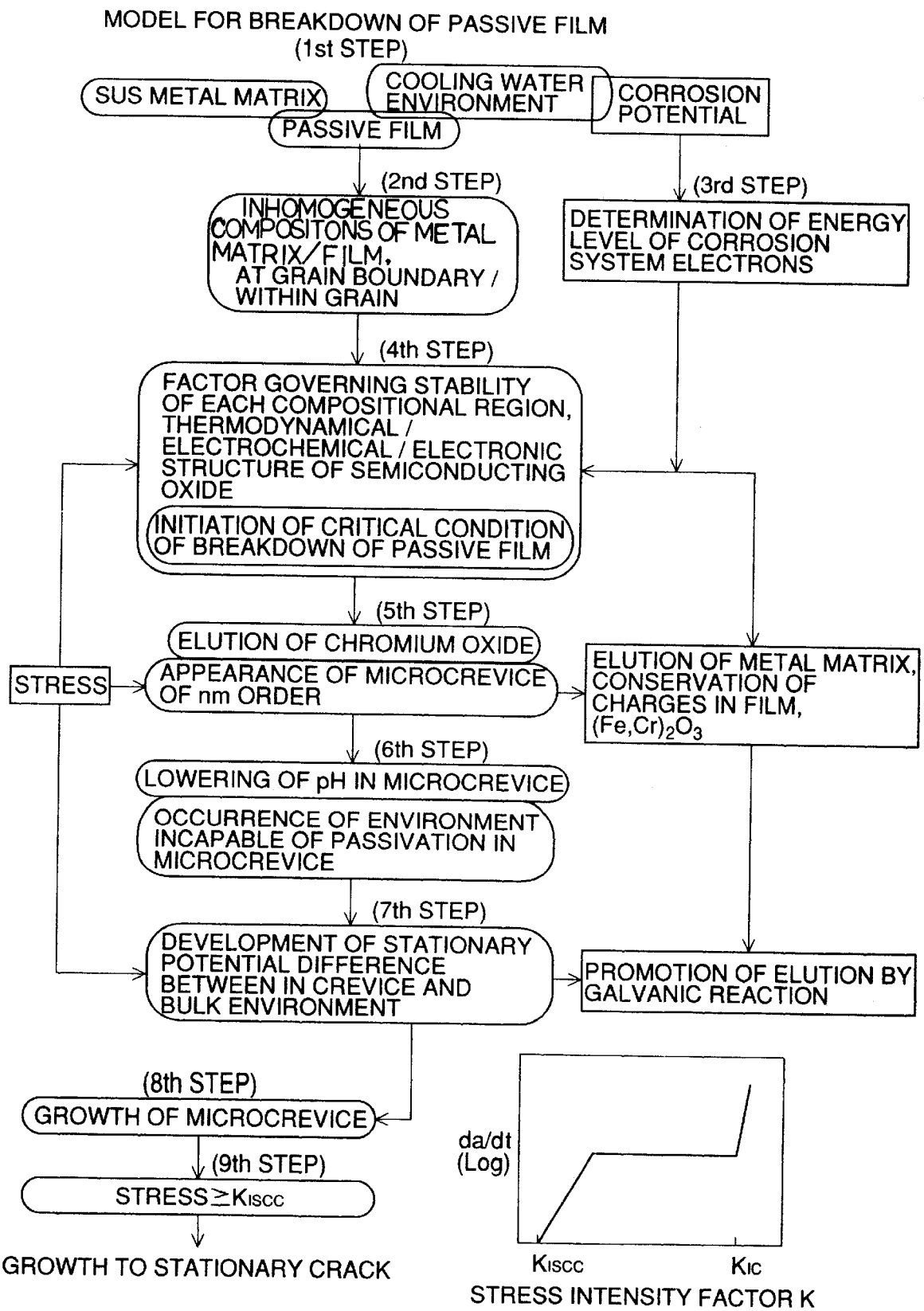

METHOD OF EVALUATING CORROSION RESISTANCE OF METAL MATERIAL, METHOD OF DESIGNING ALLOY OF HIGH CORROSION RESISTANCE, METHOD OF DIAGNOSING CORRODED STATE OF METAL MATERIAL, AND METHOD OF OPERATING PLANT

BACKGROUND OF THE INVENTION

1. Field of the Invention

The present invention relates to measuring the corrosion of a metal material. More particularly, it relates to a method of evaluating the corrosion resistance of a metal material, a method of designing an alloy of high corrosion resistance, a method of operating a plant, and a method of diagnosing the corroded state of a metal material. These methods are based on the analyzed results of a theoretical model for the corrosional damage mechanism of a plant material.

2. Description of the Related Art

The lifetime of a material in a plant directly affects that of the plant. It is therefore important, when designing a plant, to design the material and operation of the plant to reduce stress-corrosion cracking (SCC) which is especially undesirable among various types of corrosional damages of the material.

At present, techniques to be stated below are proposed as contrivances for countering SCC.

Disclosed in Japanese Patent Application Laid-open No. 333189/1993 is a technique wherein the remaining lifetime of a material which embrittles under irradiation with neutrons is measured from variations in the mechanical characteristic values of the material.

Japanese Patent Application Laid-open No. 223300/1992 discloses a method for prolonging the lifetime of a member in a newly built nuclear reactor or that of a member newly replaced in an existing nuclear reactor.

Japanese Patent Application Laid-open No. 179407/1993 discloses a method for providing a high-chromium stainless steel alloy whose SCC resistance is enhanced with respect to SCC in elevated-temperature water.

The prior-art techniques explained above are all considered as being phenomenal countermeasures to the SCC among various types of corrosional damage.

SCC is a phenomenon which arises when certain conditions of the environment, stress and material coincide. Regarding, for example, the structural material of a plant, SCC takes place initially in the case of coincidence of the conditions; (1) oxidation by oxidants (e.g., oxygen and hydrogen peroxide being those radiolytic products of water which exist in the cooling water of the plant), (2) the presence of a stress which acts on the material, and (3) the depletion or deficiency of chromium in the material. Accordingly, when any of the three elements is absent, SCC does not take place. The concentrations of oxygen etc. in the cooling water, for example, are environmental factors.

The intensity of the oxidizing power of a certain environment, in other words, the driving force thereof for the oxidation, can be indexed by a corrosion potential. As the oxidizing power of the environment is higher, the corrosion potential is higher. That is, as the corrosion potential is higher, SCC is more likely to arise. It is known, for example, that the SCC of the so-called "sensitized stainless steel", in which a chromium content at the grain boundary of the material has been lowered by carbonization of the chromium attributed to heat in a welding operation, arises at or near about −230 (mV vs. SHE (the potential of a standard hydrogen electrode)) in terms of the corrosion potential, and that it is conspicuously observed in the environment whose corrosion potential is higher.

At present, the fundamentals of the stress mode etc., the sensitized process, the basic theory, and so forth are elucidated up to a considerably high level, but phenomena at the boundary between the material and the cooling water environment (herein, especially the damaging phenomenon of the material) are not theoretically elucidated to satisfaction. It is the present situation that even the critical corrosion potential for the initiation of SCC, −230 (mV vs. SHE) as mentioned above cannot be theoretically interpreted.

In one of the prior-art techniques stated above, the critical corrosion potential for the initiation of SCC is assumed to be about −200 ((mV vs. SHE), and the oxidant concentration of the cooling water is controlled so as to render the corrosion potential thereof higher than the assumed value. However, various test conditions are involved in the experimental value (−200 mV), the significance of which is not clarified as explained above.

Accordingly, a question remains to whether or not the plant may actually be operated by setting the critical breakdown potential at −200 (mV).

If an environmental threshold value for the initiation of stress-corrosion cracking (herein, the critical corrosion potential for the initiation of SCC) can be theoretically supported, meritorious methodological approaches will be found for evaluating material, designing testing a material, for improving the environment of cooling water, etc. Heretofore, no technique has been proposed on the ground of a mechanism which uses common parameters in three regions; the corrosive environment of the material, a passive film to be formed on the material, and the metal matrix of the material.

There has not been any example in which the environmental threshold value in the breakdown of a passive film (especially, with the corrosion potential set as an index) is theoretically obtained using an electrochemical model for the semiconducting oxide film. Neither has been any example in which a method of operating a plant, a technique for designing an alloy or a technique for evaluating a corrosional damage is taught from such a viewpoint.

Incidentally, a theory for the dissolution of an ionic oxide film is disclosed in "Journal of Electrochemical Society", 113, 1067 (1966). The dissolution theory offers a theory according to which a potential gradient in an electric double layer predominates the dissolution rate of passive film, the predominance being the important point of a model for the breakdown of the passive film in the present invention. In the paper, however, the relationship of the potential gradient with a corrosional damage parameter is not stated at all, and material factors, corrosive environment factors and a stress which concern SCC are considered.

Information on the semiconducting film of an iron-chromium alloy disclosed in the Journal "Corrosion", 48, 229 (1992). It has been revealed that, when the chromium content of a semiconducting film increases, a flatband potential thereof lowers, whereupon the film exhibits more n-type characteristics. The paper, however, does not describe the relationship between the flatband potential and a corrosional damage parameter material factors, corrosive environment factors and stress which concern SCC are also not considered.

SUMMARY OF THE INVENTION

An object of the present invention is to provide a method of operating a plant, a method of evaluating corrosional damage, etc. which are based on a theoretical background, by first studying a theoretical model for factors which predominate the stability of a passive film on a metal matrix (the stability determining the durability and SCC (stress corrosion cracking) resistance of a structural material), and then generalizing a relationship among the semiconducting characteristics of the passive film, the inhomogeneous characteristics of the material, a corrosion potential and so forth.

In general, a metal material of high corrosion resistance has a rigid passive film provided on the metal matrix thereof. Even in a case where the passive film has damaged in any form, it is restored by the self-restorability thereof, and it protects the underlying metal (usually, an alloy matrix). If the passive film is stable at all times, the metal material ought not to undergo SCC irrespective of the intensity of the oxidizing power of an environment. When the oxidizing power of the environment changes, the corrosion potential thereof changes. Accordingly, if the influence of the change of the corrosion potential upon the passive film is revealed, a key to the elucidation of the reason why SCC occurs depending upon the potential will be obtained. In general, the passive film is a semiconducting oxide. Chromium oxide, etc. which predominate the corrosion resistance of stainless steel extensively used as the structural material of a plant, is a semiconducting oxides.

The inventors made studies on the critical condition of the passive film for the breakdown of the plant structural material, on the basis of an electrochemical potential at an interface at which the semiconducting oxide lies in touch with oxidants, e.g., oxygen and hydrogen peroxide as in the cooling water of the plant, an electric field structure ascribable to a band structure within the semiconductor, the elution rate of the passive film, and the inhomogeneous characteristics of the material. As a result, it has been found that the critical condition under which the passive film, after being broken down by a stress and becomes difficult to restore, does, in theory, exist. It has also been concluded that the passive film cannot be stable in a corrosive environment or at a corrosion potential which exceeds the critical condition. In other words, it has first been permitted to theoretically clarify the significance of that critical corrosion potential for the initiation of SCC which has been experimentally obtained. The present invention has been made as an application of this result.

Now, the theory forming the basis of the present invention will be detailed by taking the structural material of a BWR (boiling water reactor) plant as an example.

In a case where a corrosion system is in equilibrium, the Fermi levels of the electrons of a metal matrix, a passive film, and oxygen, hydrogen peroxide etc. in an cooling water environment become equal. FIG. 1 illustrates this situation. The meanings of symbols in the figure are as stated below. Incidentally, the energy of the electrons is set at zero in vacuum. Since the axis of ordinates in FIG. 1 represents the electron energy, the potentials of the electrons are properly multiplied by the elementary charge ($e_0$) in the figure.

$E_F$: Fermi level of the electrons

EC: Lower edge of the conduction band of the passive film

EV: Upper edge of the valence band of the passive film $\Delta\psi$: Outer potential of the passive film $X_{SC}$: Surface potential of the passive film $\mu e_0^S$: Electrochemical potential of the passive film $X_W$: Surface potential of the cooling water $\mu e_0^{RO}$: Electrochemical potential of the oxidant/reductant in the cooling water $\Delta\Phi$: Potential difference between the cooling water side and the passive film $\Delta\Phi_H$: Potential difference within an electric double layer $\Delta\Phi_{SC}$: Potential difference which develops between the interior of the passive film and the interface of the cooling water/the passive film The dissolution rate of the passive film is expressed by the exponential function of the potential difference ($\Delta\Phi_H$) within the electric double layer. Consequently, as the potential difference acting within the electric double layer is greater, the passive film being a semiconductor becomes more unstable.

In the meantime, according to the band theory of a semiconductor, the band edge is fixed (band-edge fixation principle) while the Fermi level ($E_F$) of a corrosion system lies between the conduction band and the valence band of the electrons in the passive film, in other words, within the forbidden band (EV-EC). A fluctuation in the Fermi level is entirely absorbed as the curve of the band in a space charge layer which appears in the vicinity of the surface of the oxide film. Therefore, insofar as the Fermi level ($E_F$) lies within the forbidden band (EV-EC), the potential difference ($\Delta\Phi_H$) within the electric double layer remains unchanged in spite of the fluctuation of the Fermi level.

However, when the Fermi level ($E_F$) lowers to reach the value of that band edge of the valence band of the passive film which has been fixed till then, the curve of the band in the passive film does not increase any further. Besides, when the Fermi level ($E_F$) lowers still further, the potential of the band edge having been fixed till then lowers along with the Fermi level as illustrated in the right half of FIG. 1. In this case, the surface potential ($X_W$) of the cooling water remains fixed (as defined). Therefore, that potential difference ($\Delta\Phi_H$) within the electric double layer which has been constant in spite of the fluctuation of the Fermi level till then increases to the amount of the lowering of the Fermi level. In this manner, the level (or potential) of the electrons at the band edge bounds whether or not the potential difference ($\Delta\Phi_H$) within the electric double layer is held constant.

FIG. 2 illustrates the fact that, in a case where the Fermi level of the corrosion system has fallen on the upper edge of the valence band of the passive film and has thereafter lowered $\Delta E_f$, the potential difference within the electric double layer changes from $\Delta\Phi_H$ to $E_{f2}$ (=$\Delta\Phi_H+\Delta E_f$).

In FIG. 2, symbol $E_{f1}$ denotes that Fermi level of the corrosion system which has fallen on the valence band. Symbol $E_{f2}$ denotes that Fermi level of the corrosion system down to which the Fermi level $E_{f1}$ has lowered $\Delta E_f$ (that is, up to which the corrosion potential has increased).

As already stated, the dissolution rate of the passive film is in the form of the exponential function of the potential difference ($\Delta\Phi_H$) within the electric double layer. Accordingly, when the potential difference ($\Delta\Phi_H$) within the electric double layer increases even slightly, the dissolution rate increases rapidly. That is, the stable region of the passive film is destroyed. Regarding the plant material which is to be used for a very long period of time, even a slight increase in the dissolution rate incurs serious damage with the lapse of the long time period. Herein, it is construed that the observation of the rapid increase of the dissolution rate will be ascribable to the threshold value (−230 mV vs. SHE for stainless steel) having hitherto been obtained a posteriori or empirically. The expression "stable region" signifies a region where the dissolution rate and production rate of the passive film balance each other.

Incidentally, the lowering of the Fermi level signifies the rise of the corrosion potential and the increase of the oxidizing power of the corrosive environment.

Further, according to the principle of the present invention, it is considered that the level of the valence band within the semiconducting film will differ depending upon the positions of the structural material, due to inhomogeneity in the composition of the material. In such consideration, the surface of the material is in the state in which a part that is easy to breakdown and a part that is difficult to breakdown coexist for an oxidizing power of certain intensity. As a result, the local breakdown or SCC will be initiated.

Let's apply the model of the present invention to an iron-chromium alloy by way of example. The valence band level (EV) of a chromium depletion or deficiency part at the grain boundary of the alloy lies lower in the potential level than that of a compositional region in the crystal grain of the alloy. (Note: The energy level of electrons and the potential thereof have opposite signs. Accordingly, the level EV of the chromium depletion part is higher in electron energy level.)

The valence band level of the passive film was calculated by a theoretical computation based on a molecular orbital method, while the composition ratio between iron and chromium was being changed stepwise. Then, as illustrated in FIG. 3, the valence band level EV rose with the lowering of the chromium content of the alloy. The illustrated result supports the basic theory of the present invention as described above. More specifically, the valence band level of the low chromium phase is lower in potential than that of the high chromium phase. Therefore, in a case where the oxidizing power of the environment has been intensified to lower the Fermi level (i.e., to raise the corrosion potential), the Fermi level reaches the valence band level in the low chromium phase (the critical condition) before reaching the valence band level in the high chromium phase. Consequently, only the potential difference ($\Delta\Phi_H$) of the electric double layer in the surface of the low chromium phase increases, so that only the corresponding part of the passive film is concentrically eluted. In the low chromium phase, also the re-passivation or restoration of the passive film after the breakdown thereof due to the stress becomes more difficult than in the high chromium phase. As a result, the low chromium phase suffers from local breakdown. When the Fermi level lowers still further, the potential difference ($\Delta\Phi_H$) of the electric double layer increases even in the high chromium phase. Since, however, the potential difference ($\Delta\Phi_H$) in the low chromium phase is still greater, a damage in the low chromium phase becomes much heavier similarly.

Samples of the alloy were actually prepared with the chromium content changed, and were tested. In these cases, the alloy films of lower chromium contents were more susceptible to SCC. This fact can also be explained in view of the model of the present invention for the breakdown of the passive film as stated before. Supposing that the magnitude of the chromium content of the metal matrix underlying the passive film exerts influence directly on the chromium content of the passive film, the higher chromium content of the metal matrix leads to the higher chromium content of the passive film. Besides, the upper edge of the valence band of the semiconducting oxide film of high chromium content is higher in the level (lower in the potential) than that of the valence band of the semiconducting oxide film of low chromium content. It can be concluded that these tie in with the above fact.

The present invention has been made as the application of the results of the studies by the inventors themselves as thus far described.

The corrosion potential region in which the oxide film of a metal material can stably exist in a certain oxidizing environment, can be clarified using information items which exhibit the semiconducting characteristics of the film to be formed on the surface of the material (semiconductor information items, for example, a valence band level, a band gap, a semiconductor conductivity type and a flatband potential). The semiconductor information items of the film can be obtained by the use of known photoelectrochemical techniques. The "photoelectrochemical techniques" mentioned here signify methods wherein the film is irradiated with light, and wherein a photocurrent and a potential response based on the light irradiation are analyzed. Since the methods are already well known, they shall be omitted from the description of this specification.

When applied to the design of an alloy, the present invention provides a method of designing the alloy of high corrosion resistance, in which the composition of the alloy is designed on the basis of the following guidelines a), b) and c):

a) Determining the alloy composition in which the electron energy level (EV) of the valence band of a passive film is low.

This is intended to enlarge to the utmost that fluctuating width (lowering width) of a Fermi level which is held until a potential difference ($\Delta\Phi_H$) within an electric double layer begins to increase.

b) Determining the alloy composition in which the passive film becomes an n-type semiconductor.

This comes from the fact that a p-type semiconductor has its Fermi level at a position near the electron energy level (EV) of the valence band, so the potential difference ($\Delta\Phi_H$) within the electric double layer begins to increase due to only slight lowering in the Fermi level. Since, however, the conductivity type ($\underline{n}$ or $\underline{p}$) of a semiconductor can change depending upon environments, the service environment of the alloy also needs to be taken into consideration.

c) Determining the alloy composition in which the passive film has a wide band gap.

This comes from the fact that, when the band gap is wide, the electrical resistance of the material increases, so it is difficult for current attendant upon corrosion to flow, that is, it is difficult for the corrosion to proceed.

In addition, when the semiconducting characteristics (valence band level and forbidden band width (band gap)) of the passive film of a test sample as actually measured are compared with those of the passive film of a reference sample, information items on the deterioration and corrosion resistance of the sample in the corrosive environment thereof can be obtained. In other words, a method of diagnosing the corroded state of a metal material that utilizes the information items is provided.

Further, when applied to a method of operating a plant, the present invention provides a plant operating method which controls the water chemistry (herein, oxidizing power) of plant cooling water so that the Fermi level of a corrosion system may become higher than the electron energy level of the valence band of the passive film of a material lying in touch with the cooling water (in other words, so that the film to be formed on the surface of the plant structural material may be placed in a stable potential region). Incidentally, a known method wherein a specified gas, a specified species of ions, or the like is/are injected into the plant cooling water can be applied as a practicable technique for the water chemistry control without any change.

Also realized is the kinetic handling of that dissolution of a passive film which cannot be explained by thermodynamics. Besides, regarding the initiation of SCC, the mechanism of the breakdown of the passive film is provided.

As stated before, the alloy material has the corrosion resistance which differs depending upon the positions thereof, due to the inhomogeneous composition thereof. In the alloy design or the like, accordingly, the composition of the alloy should preferably be determined with the weakest part or the lowest corrosion resistance part as a criterion. Incidentally, information which indicates the above inhomogeneity quantitatively can be obtained in such a way that the state of the composition in the surface of the material is finely evaluated or estimated using a surface analysis apparatus. Herein, when the relationship between the composition and the level of the valence band is previously obtained on the basis of, for example, the molecular orbital method, the valence band level of each position of the material can be known by comparing the result of the surface analysis with the relationship. The surface analysis apparatus (or technique) to be employed is, for example, a three-dimensional atom probe apparatus.

Moreover, corrosion can be diagnosed from a viewpoint which is quite separate from the above discussions. By way of example, the stationary crack growth rate of a metal material can be found using the potential difference between the corrosive environment and the interior of a microcrevice, information items on the growth of the microcrevice (e.g., a condition for the growth, the presence or absence of the growth, and the propagation rate of the growth), the relationships between the growth information items and a critical stress for stress corrosion cracking ($K_{1SCC}$), and so forth.

The constructions of the present invention in various aspects will be respectively stated concretely below.

In the first aspect of the present invention, there is provided a method of evaluating a corrosion resistance of a metal material in a corrosive environment concerned, wherein the metal material is formed with a passive film at its surface in the corrosive environment, the passive film making a semiconductor, comprising the steps of: finding a critical condition which is determined on the basis of information containing, at least, a valence band level of the passive film in a flatband state, and a Fermi level of a corrosion system which is constructed including the passive film and the corrosive environment, in the corrosive environment concerned; and comparing the Fermi level with the critical condition, to thereby evaluate the corrosion resistance.

In the second aspect of the present invention, there is provided a method of evaluating a corrosion resistance of a metal material in a corrosive environment concerned, wherein the metal material is formed with a passive film at its surface in the corrosive environment, the passive film making a semiconductor, comprising the steps of: finding a valence band level of the passive film in a flatband state, and a Fermi level of a corrosion system which is constructed including the passive film and the corrosive environment, in the corrosive environment concerned; and comparing the Fermi level with the valence band level, and evaluating the corrosion resistance to be higher when a width by which the Fermi level exceeds the valence band level is greater.

Herein, on condition that the valence band level of the passive film differs depending upon positions of a surface of the passive film, the comparison should preferably be made between the Fermi level and the valence band level of the highest energy level.

In the third aspect of the present invention, there is provided a method of designing an alloy of high corrosion resistance, wherein the alloy is formed with a passive film at its surface, the passive film making a semiconductor, comprising the step of determining a composition of the alloy in accordance with at least one of the following guidelines a), b) and c):

a) lowering a valence band level of the passive film in a flatband state as far as possible;
b) causing the passive film to become an n-type semiconductor; and
c) enlarging a band gap of the passive film as far as possible.

In the fourth aspect of the present invention, there is provided a method of operating a plant constructed including a metal material which is formed with a passive film at its surface in an environment included within the plant, the passive film making a semiconductor, comprising the step of controlling the environment within the plant so that a Fermi level of a corrosion system which is constructed including the passive film and the environment within the plant may become higher than a valence band level of the passive film in a flatband state, in the environment within the plant.

In the fifth aspect of the present invention, there is provided a method of diagnosing a corroded state of a metal material which is formed with a passive film at its surface, the passive film making a semiconductor, comprising the steps of: finding a valence band level of the passive film of the metal material as a test sample; and comparing the found valence band level with a valence band level of the passive film which is formed at the surface of the metal material as a reference sample, to thereby evaluate a fluctuation in a corrosion resistance of the test sample.

In the sixth aspect of the present invention, there is provided a method of diagnosing corrosion of a metal material in a certain corrosive environment, comprising the steps of: finding a potential difference between the corrosive environment and the interior of a microcrevice which is formed in a surface of the metal material; finding at least one piece of information among a condition for growth of the microcrevice, presence of the growth and a propagation rate of the growth in a state in which the potential difference develops (the information to be obtained here shall be called the "growth information" below); and finding a stationary crack growth rate of the metal material in the corrosive environment, on the basis of the growth information actually obtained and a relationship between the growth information obtained for the corrosive environment beforehand and a critical stress of the metal material for stress corrosion cracking ($K_{1SCC}$)

In the seventh aspect of the present invention, there is provided a method of diagnosing corrosion of a metal material in a corrosive environment concerned, wherein the metal material is formed with a passive film at its surface in the corrosive environment, the passive film making a semiconductor, comprising the steps of: finding a valence band level of the passive film in a flatband state, and a Fermi level of a corrosion system which is constructed including the passive film and the corrosive environment, in the corrosive environment concerned; comparing the Fermi level and the valence band level, and then finding a potential difference between the corrosive environment and the interior of a microcrevice which is formed in the surface of the metal material, on condition that the Fermi level is lower than the valence band level; finding at least one piece of information among a condition for growth of the microcrevice, presence of the growth and a propagation rate of the growth in a state in which the potential difference develops (the information to be obtained here shall be called the "growth information" below); and finding a stationary crack growth rate of the metal material in the corrosive environment, on the basis of the growth information actually obtained and a relationship between the growth information obtained for the corrosive environment beforehand and a critical stress of the metal material for stress corrosion cracking ($K_{1SCC}$)

In the eighth aspect of the present invention, there is provided a method of diagnosing corrosion of a metal material which is corroded upon contact with a corrosive environment, comprising the step of: diagnosing either of a microcracking property and passive film breakdown characteristics of the metal material from a relationship between at least one item of information from among a chemical composition of the metal material, information on a passive film to be formed on the metal material, and information on a corrosion potential of the metal material in the corrosive environment; and either of information items on a microcrack of the metal material and breakdown of the passive film of the metal material in the corrosive environment.

In the ninth aspect of the present invention, there is provided a method of designing an alloy of high corrosion resistance for a metal material which is corroded upon contact with a corrosive environment, comprising the steps of: diagnosing either of a microcracking property and passive film breakdown characteristics of the metal material from a relationship between at least one item of information from among a chemical composition of the metal material, information on a passive film to be formed on the metal material, and information on a corrosion potential of the metal material in the corrosive environment, and either of information items on a microcrack of the metal material and breakdown of the passive film of the metal material in the corrosive environment; and determining the chemical composition of the metal material on the basis of either of the diagnosed microcracking property and passive film breakdown characteristics.

In the tenth aspect of the present invention, there is provided a method of operating an equipment or industrial plant made of a metal material which is corroded upon contact with a corrosive environment; comprising the steps of: diagnosing either of a microcracking property and passive film breakdown characteristics of the metal material from a relationship between at least one information item among a chemical composition of the metal material, information on a passive film to be formed on the metal material, and information on a corrosion potential of the metal material in the corrosive environment, and either of information items on a microcrack of the metal material and breakdown of the passive film of the metal material in the corrosive environment, and controlling the corrosive environment on the basis of the diagnosed result.

In the eleventh aspect of the present invention, there is provided a method of diagnosing corrosion of a metal material which is corroded upon contact with a corrosive environment, comprising the step of: diagnosing either of a microcracking property and passive film breakdown characteristics of the metal material from a relationship between information on inhomogeneity in at least either of a chemical composition of the metal material and a passive film to be formed on the metal material, and either of information items on a microcrack of the metal material and breakdown of the passive film of the metal material in the corrosive environment.

In the twelfth aspect of the present invention, there is provided a method of diagnosing corrosion of a metal material which is exposed to a corrosive environment, comprising the step of diagnosing a stress corrosion cracking property of the metal material in the corrosive environment from a relationship between at least one item of information among a condition for elution of the metal material, a condition for appearance of a microcrevice in the metal material, a change of pH within the microcrevice, a condition for incapability of generating a passive film within the microcrevice, a potential difference between the corrosive environment and the interior of the microcrevice, and a condition for growth of the microcrevice, these information items being taken in the corrosive environment, and stress corrosion cracking characteristics of the metal material in the corrosive environment.

In the thirteenth aspect of the present invention, there is provided a method of designing an alloy of high corrosion resistance for a metal material which is exposed to a corrosive environment, comprising the steps of: diagnosing a stress corrosion cracking property of the metal material in the corrosive environment from a relationship between at least one item of information among a condition for elution of the metal material, a condition for appearance of a microcrevice in the metal material, a change of pH within the microcrevice, a condition for incapability of generating a passive film within the microcrevice, a potential difference between the corrosive environment and the interior of the microcrevice, and a condition for growth of the microcrevice, these information items being taken in the corrosive environment, and stress corrosion cracking characteristics of the metal material in the corrosive environment; and determining a chemical composition of the metal material on the basis of the diagnosed result.

In the fourteenth aspect of the present invention, there is provided a method of operating an equipment or industrial plant made of a metal material which is corroded upon contact with a corrosive environment, comprising the steps of: diagnosing a stress corrosion cracking property of the metal material in the corrosive environment from a relationship between at least one item of information from among a condition for elution of the metal material, a condition for appearance of a microcrevice in the metal material, a change of pH within the microcrevice, a condition for incapability of generating a passive film within the microcrevice, a potential difference between the corrosive environment and the interior of the microcrevice, and a condition for growth of the microcrevice, these information items being taken in the corrosive environment, and stress corrosion cracking characteristics of the metal material in the corrosive environment; and controlling the corrosive environment on the basis of the diagnosed result.

In the fifteenth aspect of the present invention, there is provided a method of diagnosing corrosion of a metal material, comprising: the first step of finding a chemical composition of the metal material, information on a passive film to be formed on the metal material, information on a corrosive environment, and information on a corrosion potential of the metal material in the corrosive environment; the second step of finding at least one item of information from among inhomogeneity in the chemical composition of the metal material, inhomogeneity in the passive film of the metal material, and inhomogeneities in compositions of the metal material at a grain boundary and within a grain boundary; the third step of finding an energy level of electrons in a corrosion system on the basis of the corrosion potential, the corrosion system being constructed including the passive film and the corrosive environment; the fourth step of finding a critical condition for breakdown of the passive film on the basis of the information items obtained in the second step and the third step; the fifth step of finding either of a condition for elution of the metal material and a condition for appearance of a microcrevice in the metal material on the basis of the information obtained in the fourth step; the sixth step of finding either of a change of pH within the microcrevice and a condition for incapability of generating the passive film within the microcrevice, on the basis of the information obtained in the fifth step; the seventh step of finding a potential difference between the corrosive environment and the interior of the microcrevice on the basis of the information obtained in the sixth step; the eighth step of finding at least one item of information from among a condition for growth of the microcrevice, presence of the growth and a propagation rate of the growth, on the basis of the information obtained in the seventh step; and the ninth step of finding a condition for stationary crack growth in the metal material, from a relationship between the information obtained in the eighth step and a critical stress of the metal material for stress corrosion cracking thereof in the corrosive environment.

In the sixteenth aspect of the present invention, there is provided a method of designing an alloy of high corrosion resistance for a metal material, comprising: the first step of finding information on a corrosive environment of the metal material, and information on a corrosion potential of the metal material in the corrosive environment; the second step of finding at least one item of information from among inhomogeneity in a chemical composition of the metal material, inhomogeneity in a passive film to be formed on the metal material, and inhomogeneities in compositions of the metal material at a grain boundary and within a grain boundary; the third step of finding an energy level of electrons in a corrosion system on the basis of the corrosion potential, the corrosion system being constructed including the passive film and the corrosive environment; and the fourth step of determining a composition of the alloy on the basis of the electron energy level of the corrosion system as obtained in the third step, so that a corrosion potential range previously set for a service environment condition of the metal material and a Fermi level range of the electrons may lie between a conduction band and a valence band of electrons in a semiconductor electronic structure of the passive film or oxide film of the metal material.

In the seventeenth aspect of the present invention, there is provided a method of operating a plant such as a nuclear or thermal power plant or a chemical plant, wherein ions are injected into cooling water of the plant so as to prevent corrosional damage of a metal material which lies in contact with the cooling water, comprising: the first step of finding information on the corrosive environment of the metal material, and information on a corrosion potential of the metal material in the corrosive environment; the second step of finding at least one item of information among inhomogeneity in a chemical composition of the metal material, inhomogeneity in a passive film to be formed on the metal material, and inhomogeneities in compositions of the metal material at a grain boundary and within a grain boundary; the third step of finding an energy level of electrons in a corrosion system on the basis of the corrosion potential, the corrosion system being constructed including the passive film and the corrosive environment; and the fourth step of determining a quantity of ion injection into the cooling water, on the basis of the electron energy level of the corrosion system as obtained in the third step, so that a corrosion potential range previously set on the basis of a service environment condition of the metal material and a Fermi level range of the electrons may lie between a conduction band and a valence band of electrons in a semiconductor electronic structure of the passive film or oxide film of the metal material.

Now, the operations of the various aspects of the present invention will be described.

The first thru fifth aspects operate as stated below.

A stable corrosion potential region for the passive film to be formed on the surface of the metal material can be found in the corrosive environment (oxidizing environment) in which the metal material is placed, on the basis of the semiconducting characteristics of the passive film (for example, the level of the valence band, the band gap, the semiconductor conductivity type and the flatband potential, especially the valence band level versus a reference electrode). Accordingly, the alloy can be designed with the semiconducting characteristics as the guidelines. Moreover, it is possible to know a water chemistry environment in which the metal can exist stably. Using the knowledge of the water chemistry environment, the plant operation can be managed at a high reliability and at a higher precision for predictive maintenance. Further, the fluctuation of the corrosion resistance, etc. of the test sample can be evaluated by comparing the semiconducting characteristics with those of the reference sample.

In addition, when sensitization characteristics are clarified, a specified part can be indicated as being secure against corrosional damage.

The sixth aspect operates as stated below.

The potential difference is found between the corrosive environment and the interior of a microcrevice which is formed in the surface of the metal material. Incidentally, in a case where the potential difference is difficult to actually measure, a potential may well be measured for a gap or the like simulative of the crevice, so as to handle the measured result as the potential difference. Subsequently obtained is the information on the growth of the microcrevice corresponding to the potential difference (at least one information item among the condition for the growth, the presence of the growth and the propagation rate of the growth).

The "condition for the growth" signifies the shape of the crevice, etc.

The "presence of the growth" (in other words, whether or not the crevice grows) can be presumed using, e.g., the statistical analysis of an extreme value.

The "propagation rate of the growth" can be obtained using any of various empirical formulae.

The growth information obtained in this way is compared with the relationship between it and the critical stress ($K_{1SCC}$) of the metal material for the stress corrosion cracking (SCC). Thus, the stationary crack growth rate of the metal material can be found. Incidentally, the relationship between the growth information and the critical stress ($K_{1SCC}$) for the SCC may be found e.g., experimentally and then stored as a database beforehand.

Regarding the actual application of the sixth aspect, it is more preferable that, as in the seventh aspect, the stationary crack growth rate is found as required by applying the sixth aspect after the diagnosis in the first or second aspect has been carried out.

The operations of the eighth thru seventeenth aspects are basically the same as those of the aspects stated above.

BRIEF DESCRIPTION OF THE DRAWINGS

FIG. 4 is a diagram showing the outlines of a process for the breakdown of a passive film and a method of evaluating corrosion;

PREFERRED EMBODIMENTS OF THE INVENTION

The embodiments of the present invention will be described with reference to the accompanying drawings.

The overall process of the formation and breakdown of a passive film at the surface of a structural material can be indicated by a flow shown in FIG. 4. The corrosion of the structural material can be diagnosed by studying the process wholly or partly. An example in which a study was especially made on the fourth step of the process holding the key to the breakdown of the passive film, to find appropriate plant operating conditions, will be described as Embodiment 1. Another example in which studies were similarly made on the fifth thru ninth steps, will be described as Embodiment 2. Data to be mentioned in the ensuing description were actually obtained by the sampling and photoelectrochemical experiments of actual plant materials.

Embodiment 1

Figure 5A:
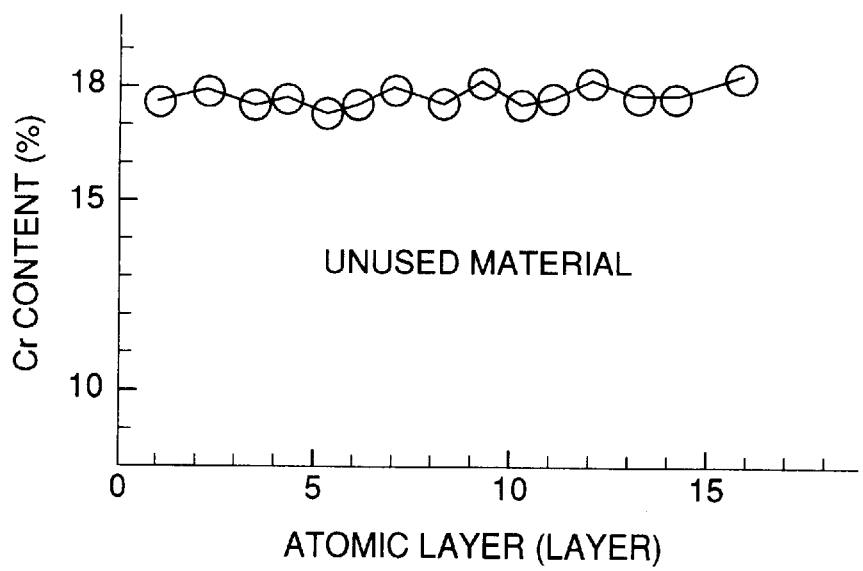
FIGS. 5A and 5B are graphs showing chromium content distributions in the minute regions of an unused material and an actual plant material in the first embodiment of the present invention, respectively.
Figure 5B:
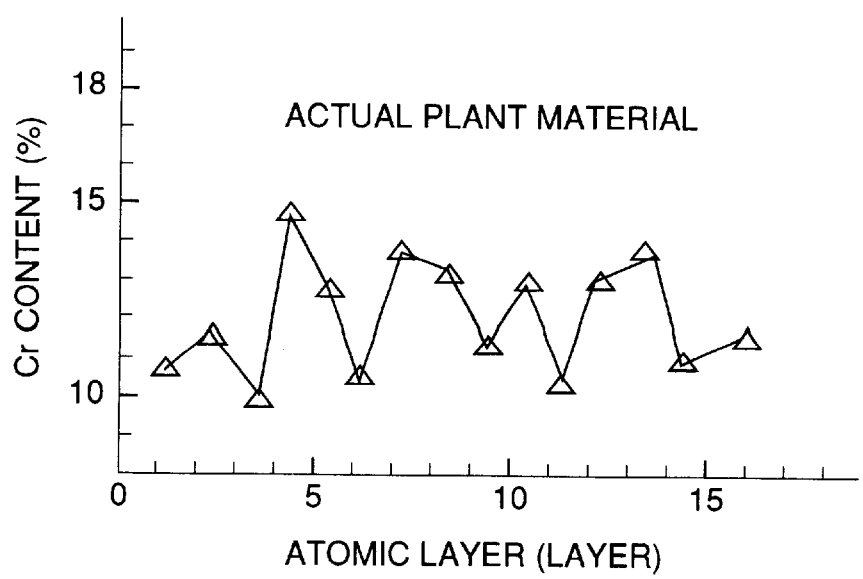

Shown in FIG. 5B is a result which was obtained by investigating the change of the chromium content of the structural material (stainless steel SUS304) of an actual nuclear power plant after the 30-year operation of the plant. For the sake of comparison, the analyzed result of an unused material is shown in FIG. 5A. Incidentally, a method of sampling the structural material used in this embodiment will be described later with reference to FIG. 13, and a method of analyzing the structural material with reference to FIGS. 14 and 15.

In the unused material, the chromium content is substantially constant at 18 (%) even at the level of atomic regions (refer to FIG. 5A).

On the other hand, in the actual plant material, as seen from FIG. 5B, the chromium content is discrepant (that is, the composition of the material is inhomogeneous) at substantially every minute region (at the atomic level). Besides, although the chromium content differs depending upon places, its value having been 18 (%) at the start of the operation of the plant lowers down to 12 (%) on average. The chromium content lowering corresponds exactly to the chromium content of a thermally sensitized part.

Therefore, an iron/nickel/chromium alloy having an alloy composition of Fe-8Ni-12Cr was prepared by simulating the composition of the stainless steel after the secular change, and the semiconducting characteristics of a passive film formed at the surface of the prepared alloy were investigated by a photoelectrochemical experiment in pressurized and elevated-temperature water at 290 (°C.). For the sake of comparison, a similar experiment was also conducted on the Fe-8Ni-18Cr steel whose chromium content did not lower. Hereinbelow, the Fe-8Ni-12Cr alloy prepared by simulating the composition of the stainless steel after the secular change shall be simply called the "12Cr steel". Likewise, the Fe-8Ni-18Cr steel shall be called the "18Cr steel".

The photoelectrochemical experiments were conducted by a conventional method stated below.

Details of Photoelectrochemical experiment

A working (or sample) electrode was put in an autoclave having a sapphire window, and the autoclave was held in the pressurized and elevated-temperature water at 290 (°C.). Currents, potentials etc. were measured while the working electrode was being irradiated with light.

The working electrode used had a geometric surface area of 1 ($cm^2$). A Pt (platinum) electrode of 1 ($cm^2$) was employed as a counter electrode. A saturation solubility type Ag/AgCl (silver/silver chloride) electrode was employed as a reference electrode. The SHE (standard hydrogen electrode) calculation of the Ag/AgCl electrode was based on known data.

Light for irradiating the working electrode was white light emitted from a xenon lamp of 1 (kW), or was monochromatic light obtained by passing the white light through a diffraction grating type monochrometer. An irradiating photon flux at each wavelength of the monochromatic light was held constant in such a way that the quantity or energy of the irradiating light was monitored with a thermocouple sensor, and that the light transmission coefficient of a filter was feedback-controlled. The light emergent from the light source was switched by an electromagnetic shutter, and was caused to irradiate the sample through the sapphire window.

The time-based change of the current generated by the light irradiation was recorded by an oscilloscope and a recorder. The potential was controlled using an ordinary potentiostat of differential amplifier type. The output signal of a zero-shunt ammeter was amplified as a current signal.

The results of such photoelectrochemical experiments are illustrated in FIGS. 6 thru 10. The experimental results in FIGS. 6 thru 8 concern the 12Cr steel, while the experimental results in FIGS. 9 and 10 concern the 18Cr steel.

Figure 6:
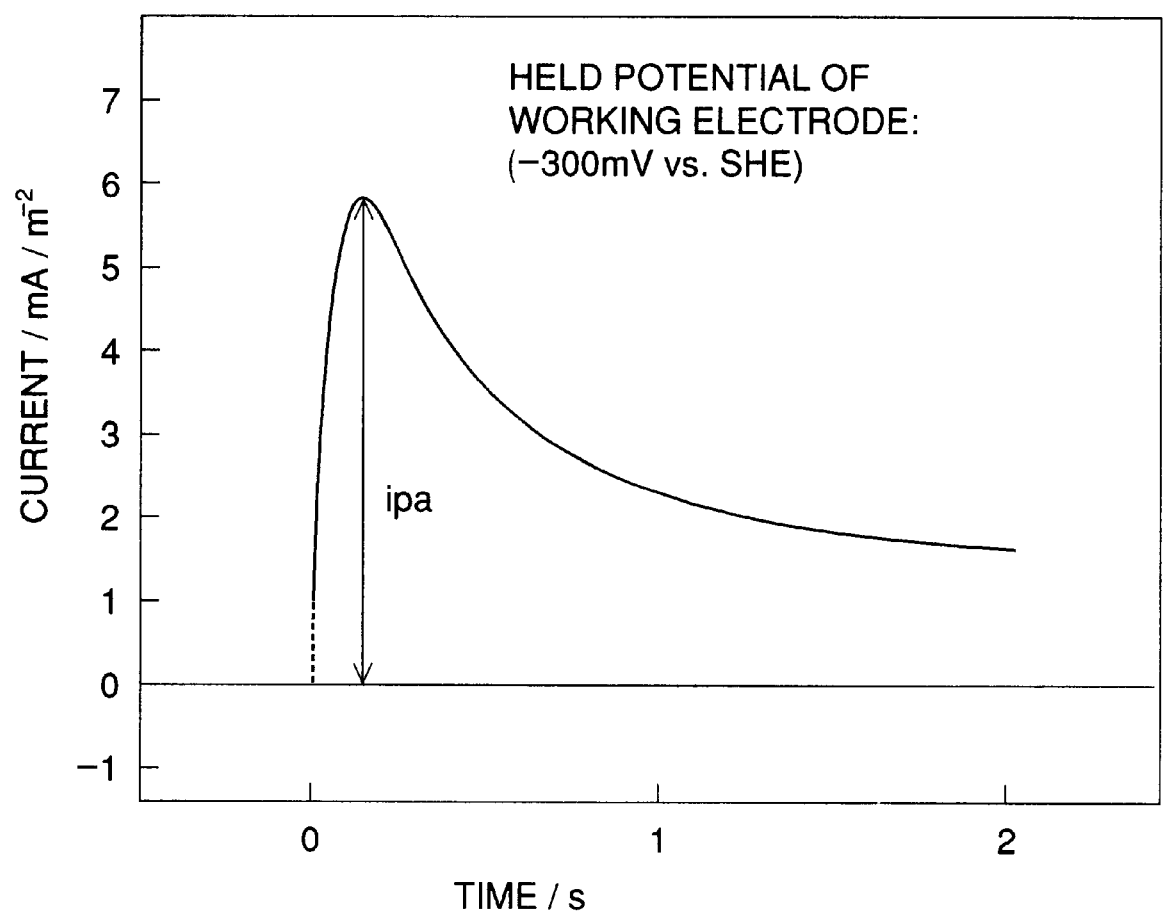
FIG. 6 is a graph showing the curve of the time-based change of a photocurrent ($i_{pa}$) in an Fe-8Ni-12Cr alloy (at 290° C.)

FIG. 6 shows the photoelectrochemical response of the sample obtained by irradiating this sample with the white light of the xenon lamp. Since the photocurrent ipa is positive, it has been revealed that the passive film of the sample is an n-type semiconductor.

Figure 7:
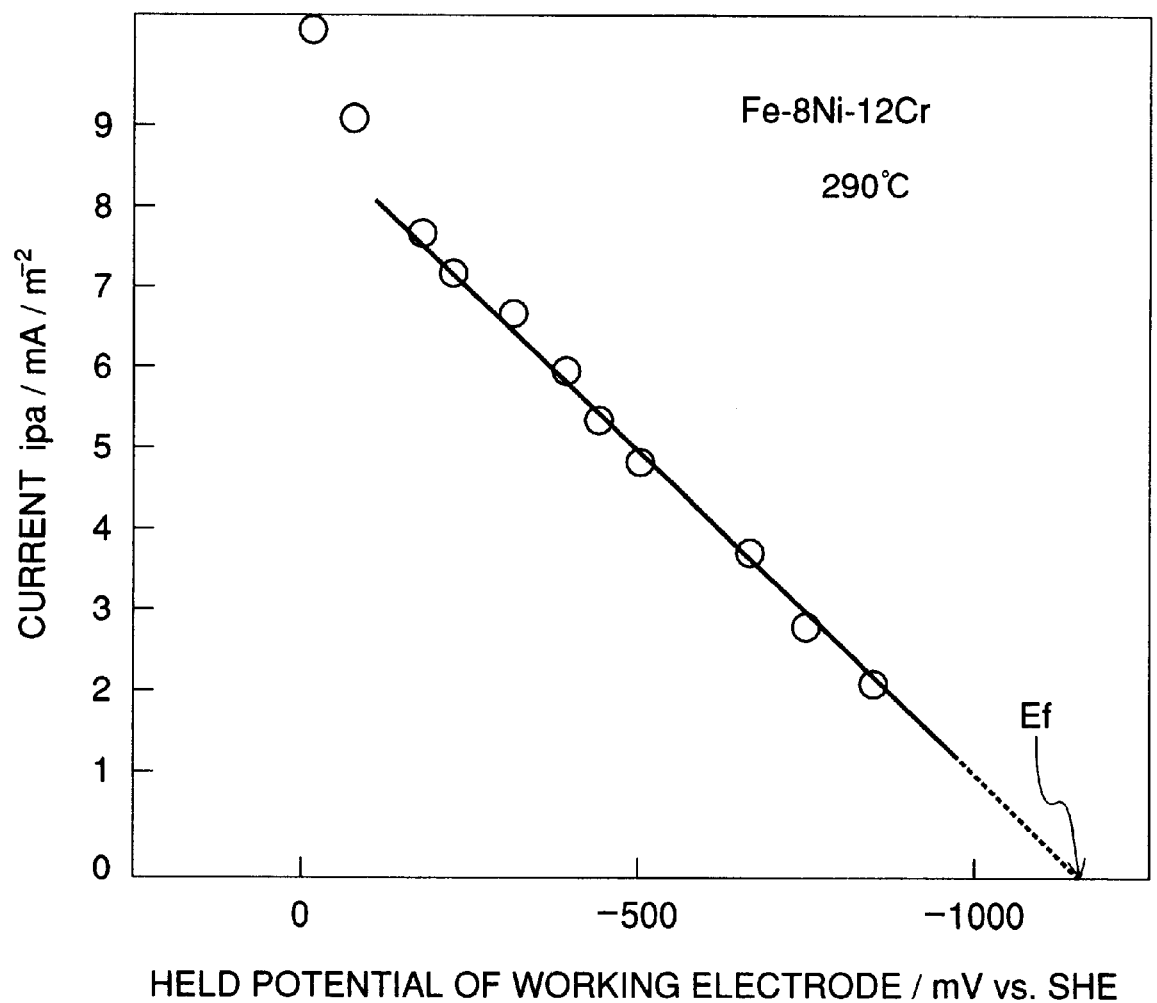
FIG. 7 is a graph showing the working electrode potential-dependency and the flatband potential ($E_f$) of the photocurrent ($i_{pa}$) in the Fe-8Ni-12Cr alloy.

FIG. 7 shows the measured result of the relationship between the held potential of the sample and the current ($i_{pa}$). It is thought by the extrapolation of the experimental result that the potential at which the current ($i_{pa}$) becomes zero will be about −1160 (mV vs. SHE (standard hydrogen electrode)). It is accordingly thought that the flatband potential of the sample material (12Cr material) will be about −1160 (mV vs. SHE).

Figure 8:
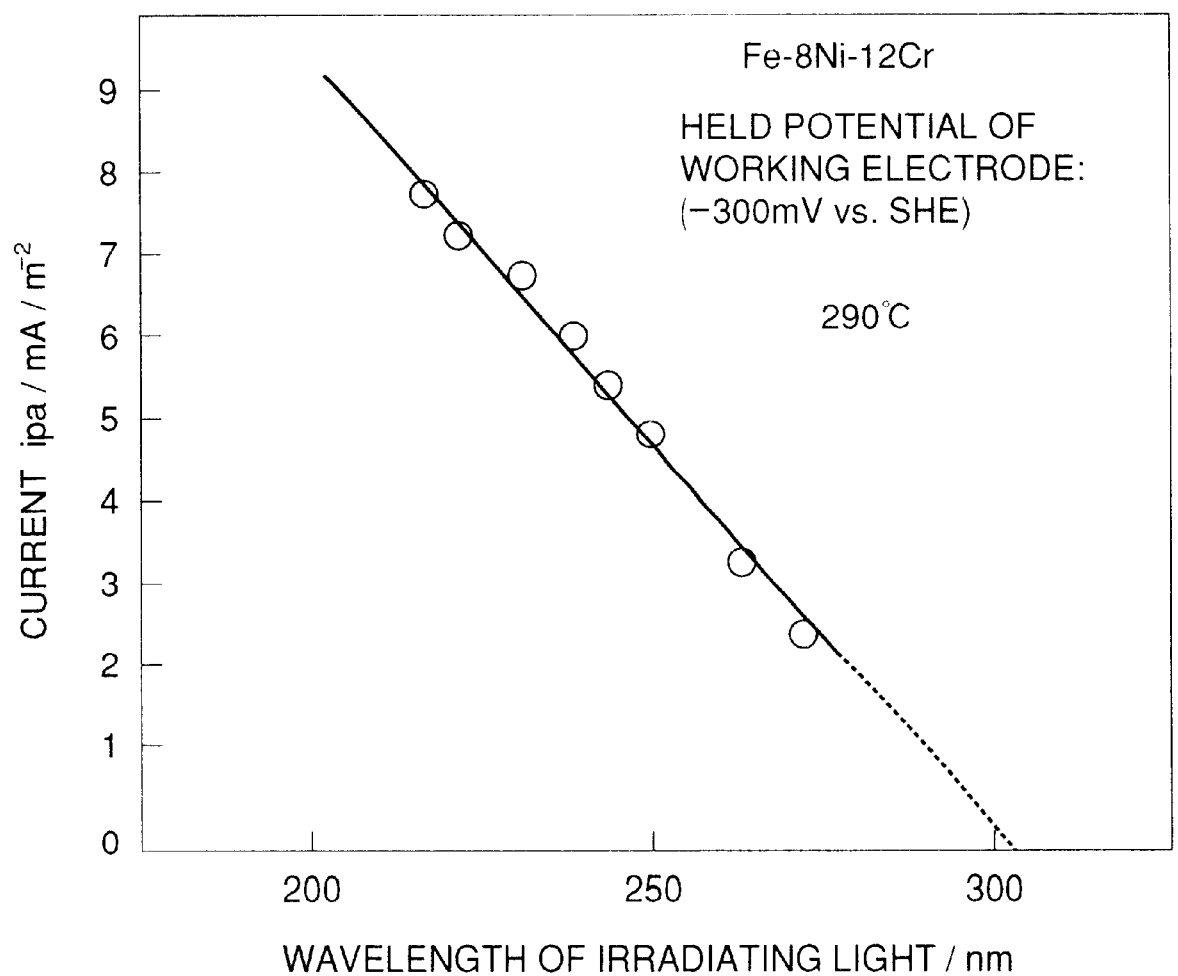
FIG. 8 is a graph showing the irradiating light wavelength-dependency of the photocurrent ($i_{pa}$) in the Fe-8Ni-12Cr alloy.
Figure 9:
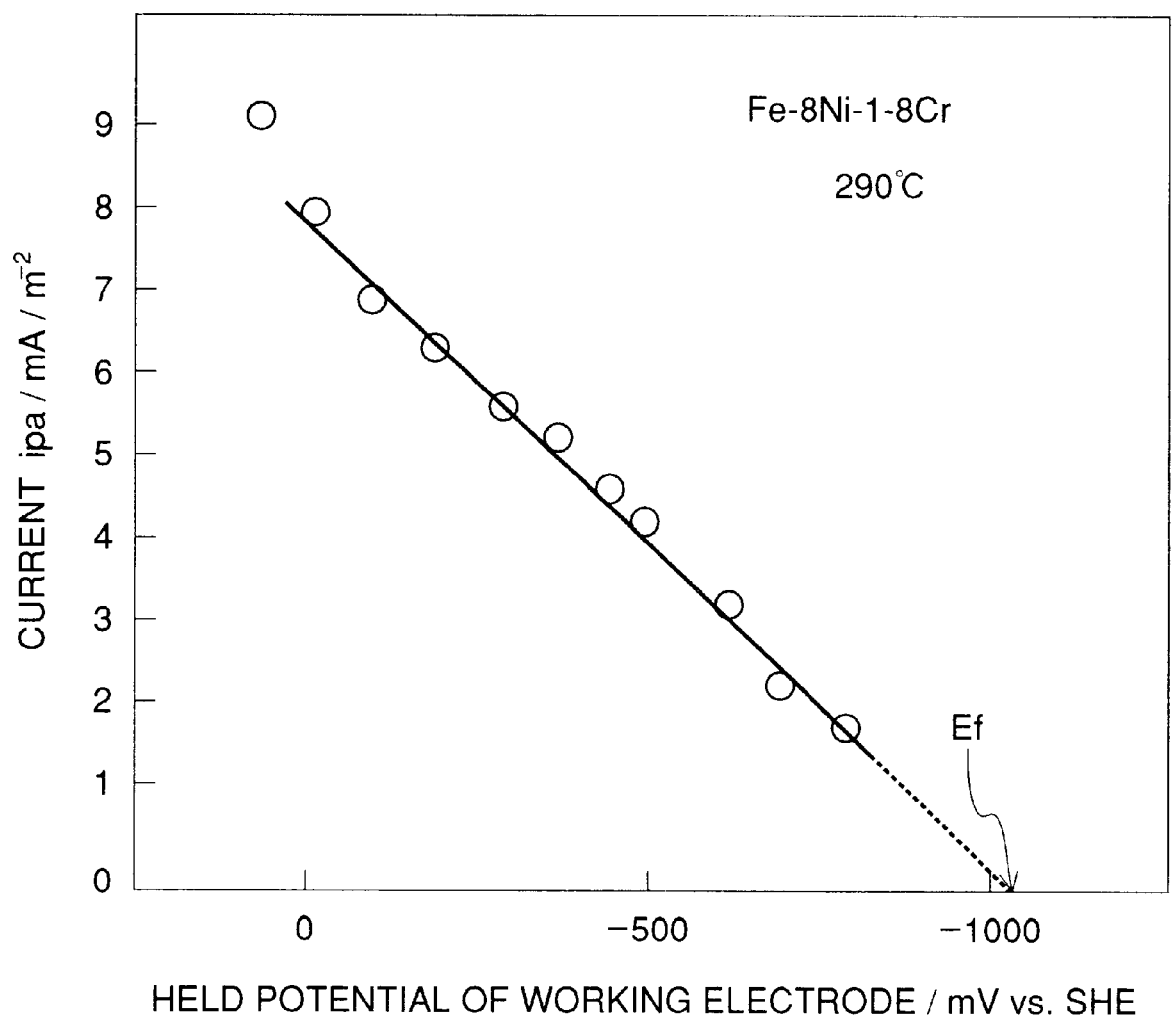
FIG. 9 is a graph showing the working electrode potential-dependency and the flatband potential ($E_f$) of a photocurrent ($i_{pa}$) in an Fe-8Ni-18Cr alloy.
Figure 10:
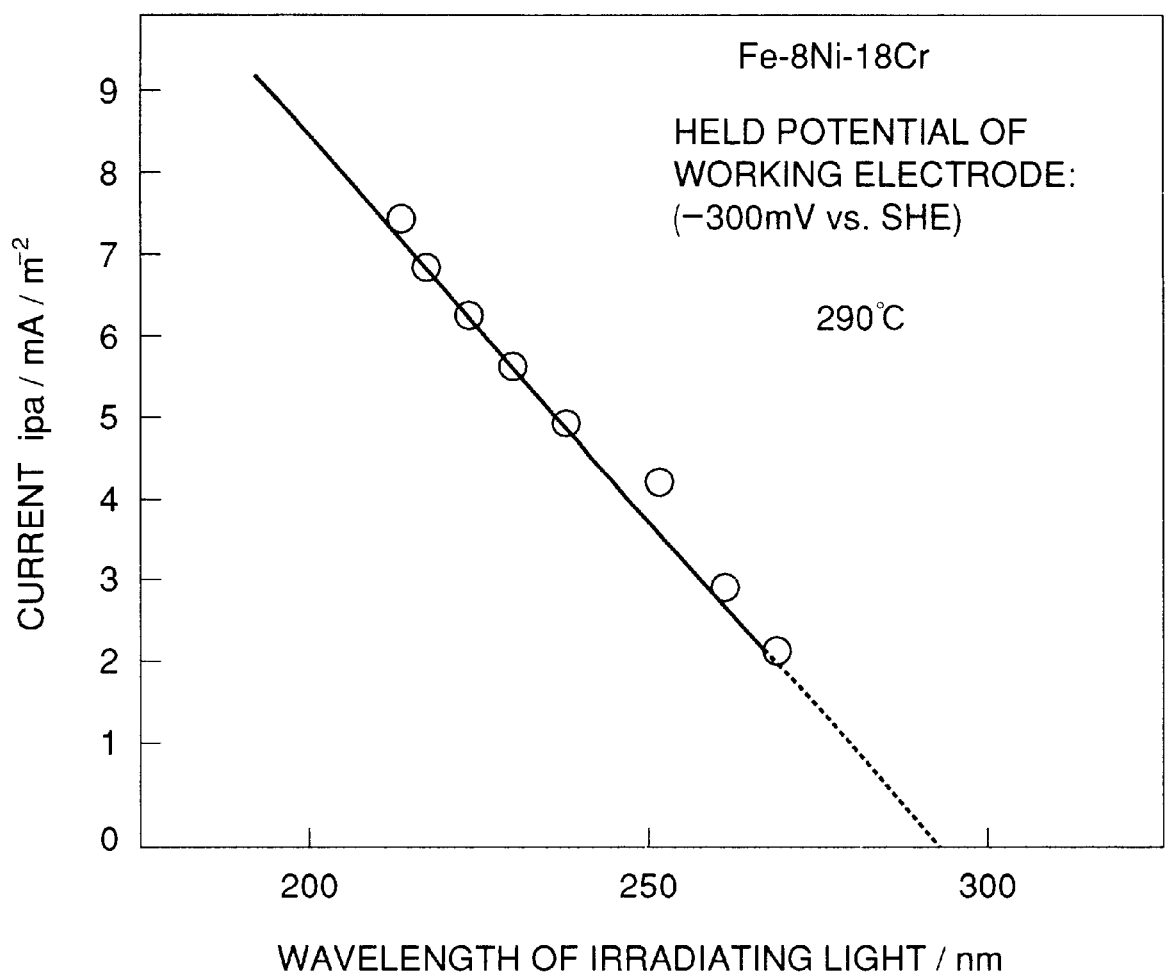
FIG. 10 is a graph showing the irradiating light wavelength-dependency of the photocurrent ($i_{pa}$) in the Fe-8Ni-18Cr alloy.

FIG. 8 shows the measured result of the relationship between the wavelength of the irradiating light and the current ($i_{pa}$). Since the absorption wavelength at which the current ($i_{pa}$) disappears is about 310 (nm), it has been revealed that the passive film of the sample simulative of the actual plant material has a band gap of about 1.0 (eV).

When the 18Cr steel was also submitted to the similar experiment, the passive film formed at the surface thereof was an n-type semiconductor. Besides, the flatband potential and band gap of the 18Cr steel were about −1000 (mV vs. SHE) and about 1.1 (eV) as seen from FIG. 9 and FIG. 10, respectively.

Figure 1:
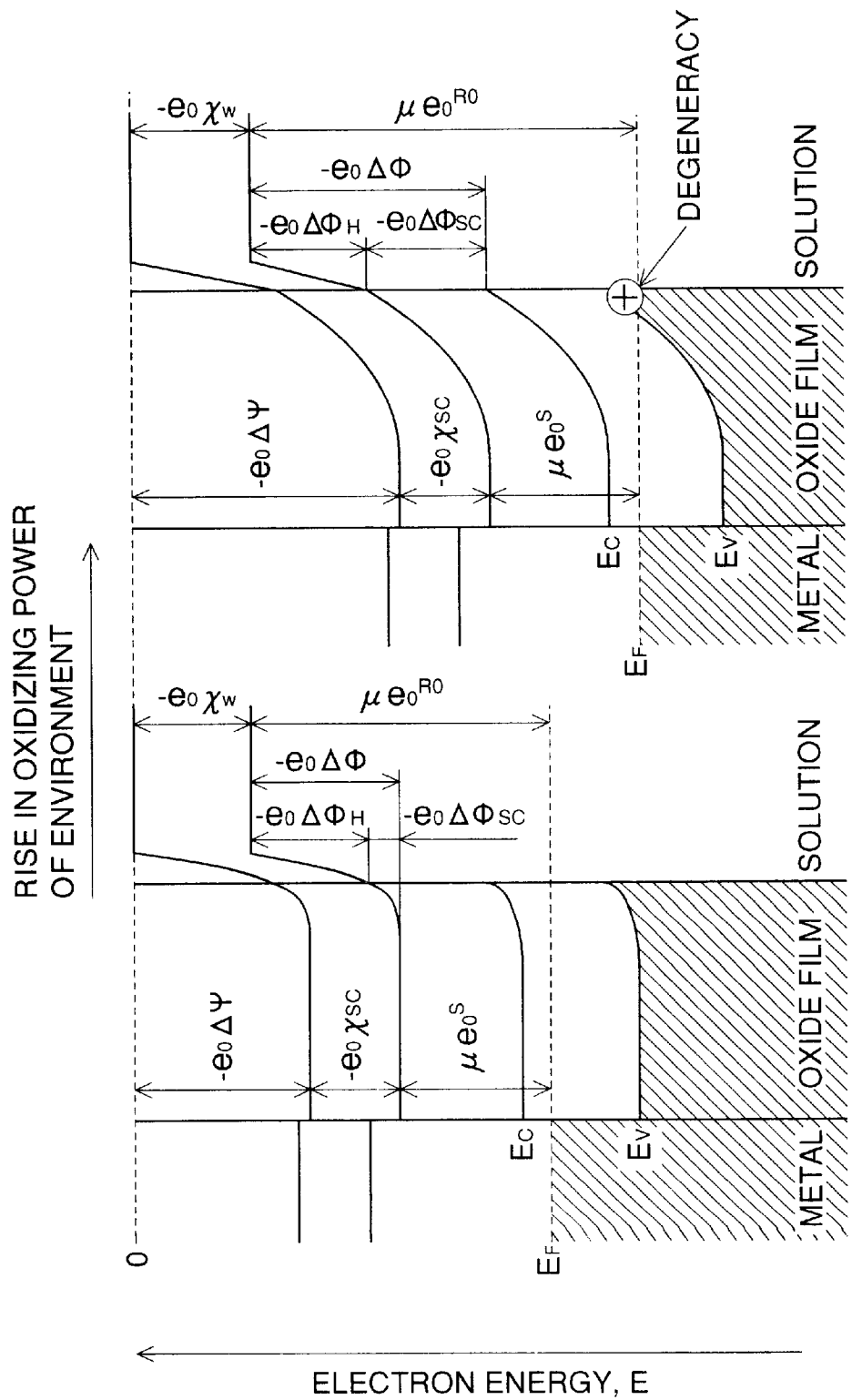
FIG. 1 is a model diagram of a band structure at the interface between a semiconductor and cooling water.
Figure 2:
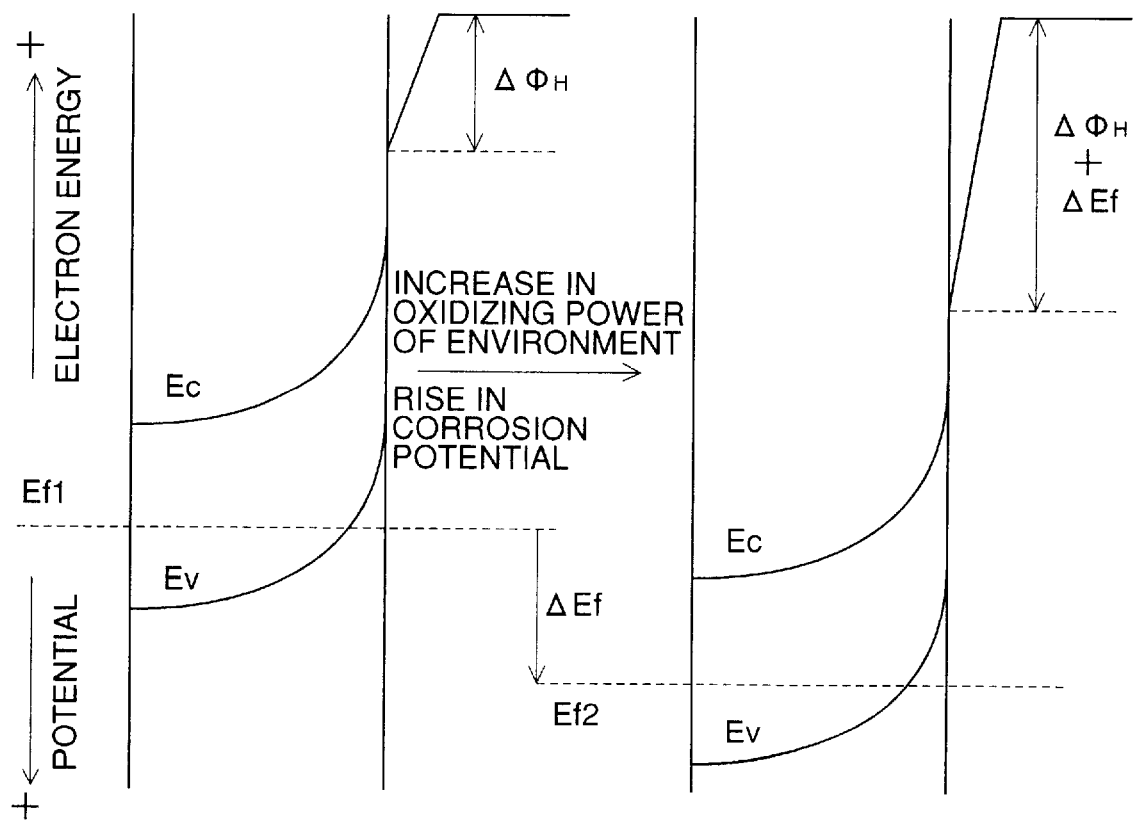
FIG. 2 is a model diagram showing that change of an electric field within an electric double layer which is attendant upon a corrosion potential rise after a Fermi level has fallen on a valence band.
Figure 3:
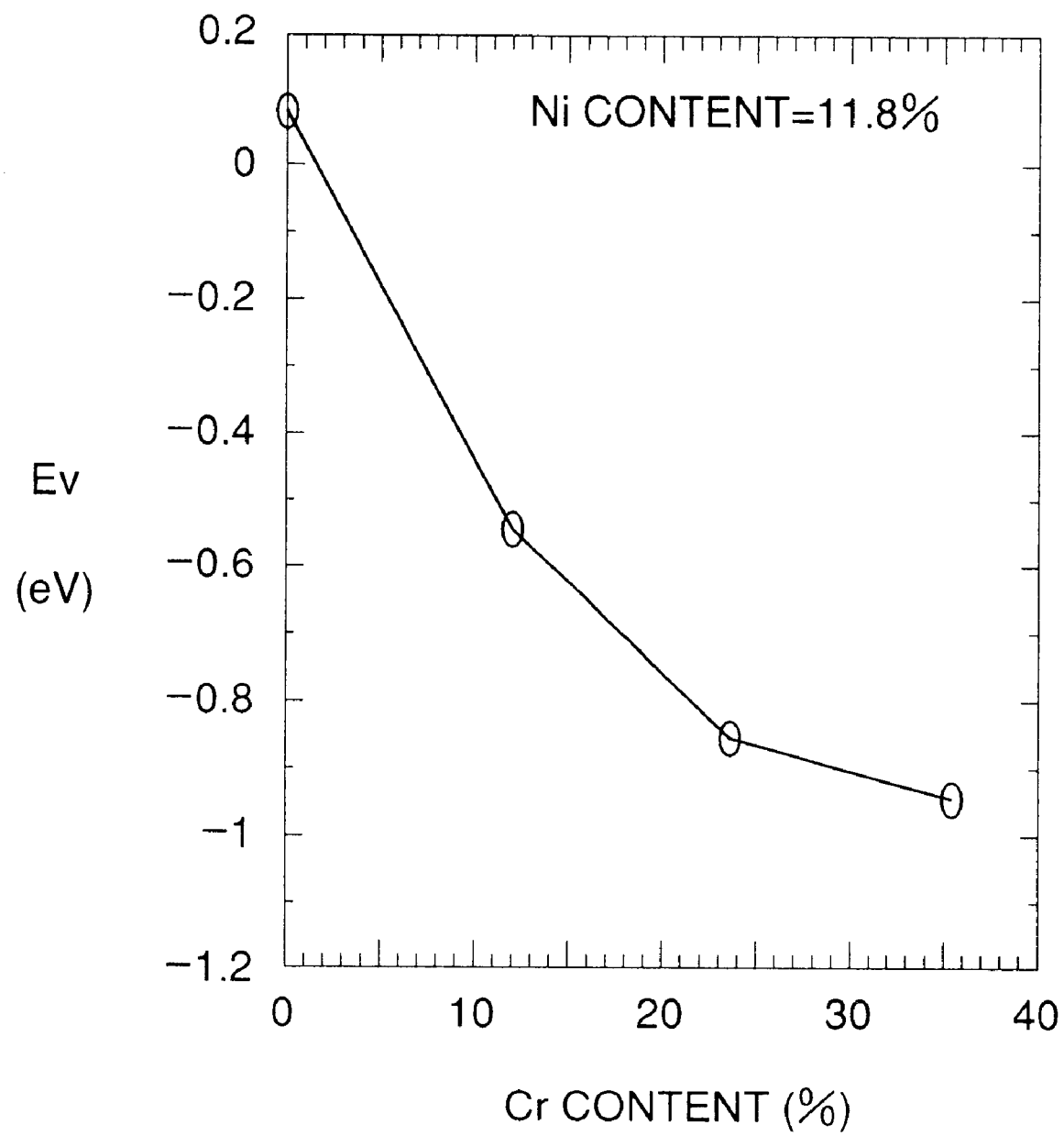
FIG. 3 is a graph showing that result of the relationship between the chromium content of an Fe—Ni—Cr oxide film and the valence band level thereof which has been theoretically computed using a molecular orbital method.

The valence band level of a material can be found by adding the flatband potential (in energy units of eV) to the band gap (refer to FIG. 1). Accordingly, when computed with the above experimental data, the valence band level of the 12Cr steel results in about −160 (mV) with respect to the potential of the SHE. Likewise, the valence band level of the 18Cr steel results in about +100 (mv) with respect to the potential of the SHE. As the valence band level of the passive film, the 12Cr steel (the material having undergone the secular change) is lower by about 260 (mV) in terms of the potential. That is, the potential allowance of the 12Cr steel is about 260 (mV) lower compared with that of the 18Cr steel (the material before the operation of the plant). This fact is construed as stated below. Since the plant is operated in the state of a corrosion potential of +80 (mV vs. SHE), the passive film will have been held in its stable region at the initial stage of the plant operation. After the 30-year operation, however, the whole of the passive film will be in its unstable region. That is, the corrosion potential lies in the region which greatly exceeds the potential of the valence band of the passive film of the deteriorated material. Consequently, a potential gradient enlarges within an electric double layer at the interface between the deteriorated material and the cooling water of the plant, and the possibility of the local breakdown of the passive film is very high.

As stated before, the chromium content at the surface of the actual structural material is greatly discrepant and is inhomogeneous (refer to FIG. 5B). The whole surface of the structural material does not have the composition corresponding to the 12Cr steel, but the inhomogeneity is merely observed in the minute regions. As already explained, however, the stress corrosion will be initiated with its start point at any of the local parts corresponding to the 12Cr steel. Accordingly, information items on the different material properties of the passive film at the inhomogeneous material surface cannot be ignored in continuing the plant operation.

It has been revealed from the above experimental results that, in the Fe—Ni—Cr alloy, the valence band level of the passive film rises (the potential thereof lowers) due to the lowering of the chromium content. In the design of an alloy containing chromium, accordingly, the alloy needs to be designed in the direction of increasing the chromium content thereof. Even in a case where the other constituents of the alloy are changed, the algorithm (design guideline) of the present invention is applicable as it is.

In the plant which is a subject for the above study and in which the term of 30 years has lapsed since the start of the operation, safety can be secured in such a way that the corrosion potential is controlled to or below −160 (mV) by lowering the concentrations of oxidants, e.g., oxygen and hydrogen peroxide, in the cooling water. In this regard, an example in which the corrosion potential is lowered by injecting hydrogen into the feed water system of the plant as a countermeasure to SCC (stress corrosion cracking) will be described with reference to FIGS. 11 and 12.

Figure 11:
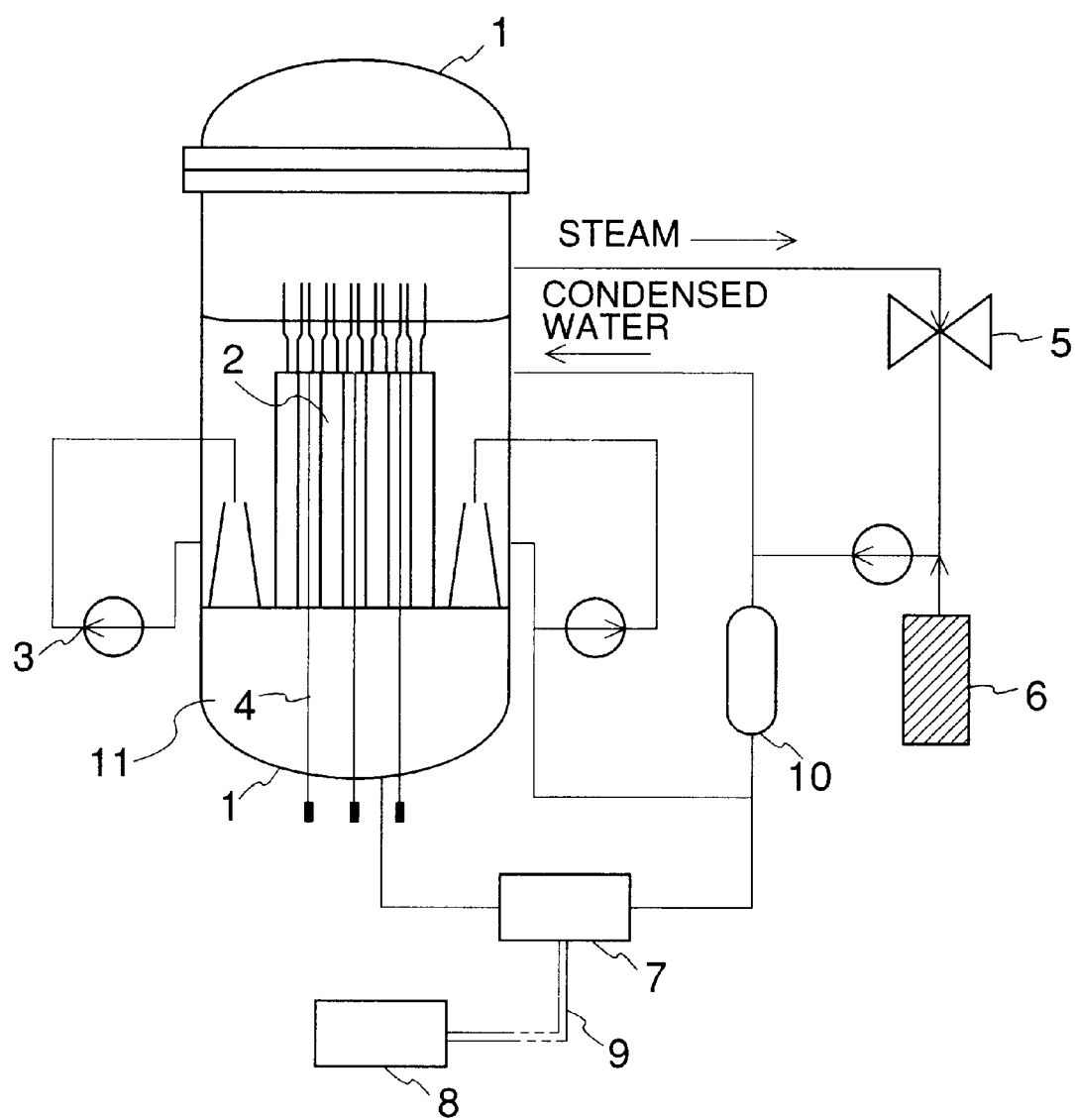
FIG. 11 is a schematic block diagram showing the outlines of a corrosion potential measurement system and a hydrogen injection system for a BWR plant.

FIG. 11 is a schematic block diagram of a corrosion potential measurement system and a hydrogen injection system for a boiling water reactor (BWR) plant. In the figure, numeral 1 designates a pressure vessel, numeral 2 fuel, numeral 3 a recirculation system, numeral 4 a control rod, numeral 5 a condensing turbine, numeral 6 a hydrogen injection device, numeral 7 a corrosion potential measurement device, numeral 8 a control room, numeral 9 a signal cable, numeral 10 a reactor water cleanup device, and numeral 11 the bottom of the pressure vessel 1.

Figure 12:
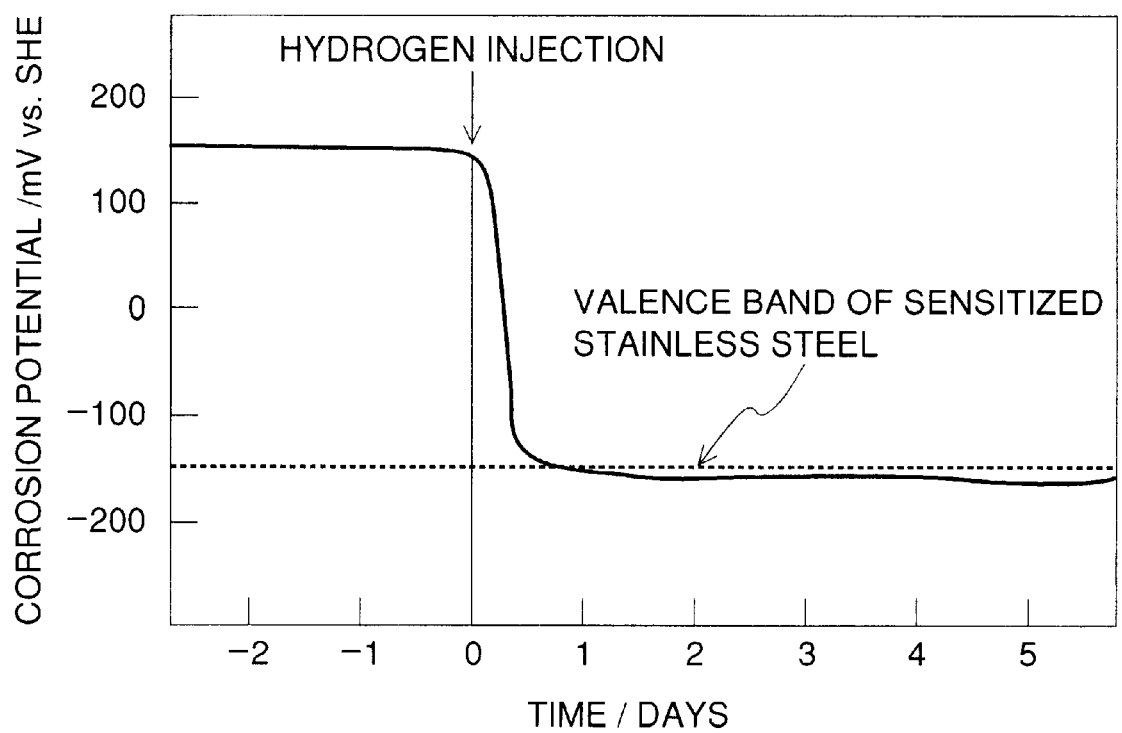
FIG. 12 is a graph showing the situation of that change of a corrosion potential at the bottom of a reactor pressure vessel which is based on the injection of hydrogen into the feed water system of the BWR plant.

FIG. 12 illustrates a result obtained by monitoring the potential signal of the corrosion potential sensor (7 in FIG. 11) which was mounted in the reactor water cleanup system of the plant. When hydrogen at about 300 (ppb) was injected into the feed water system of the plant, the corrosion potential of the deterioration simulating material (Fe-8Ni-12Cr) located at the pressure vessel bottom (11 in FIG. 11) became below −160 (mV). This fact has revealed that, as the concentration of the hydrogen to be injected into the feed water system, the concentration of 300 (ppb) as measured in feed water is the lowest injection concentration. It has been determined that the BWR plant should be continuously operated thenceforth by setting the hydrogen concentration of the feed water system at about 350 (ppb).

Figure 13:
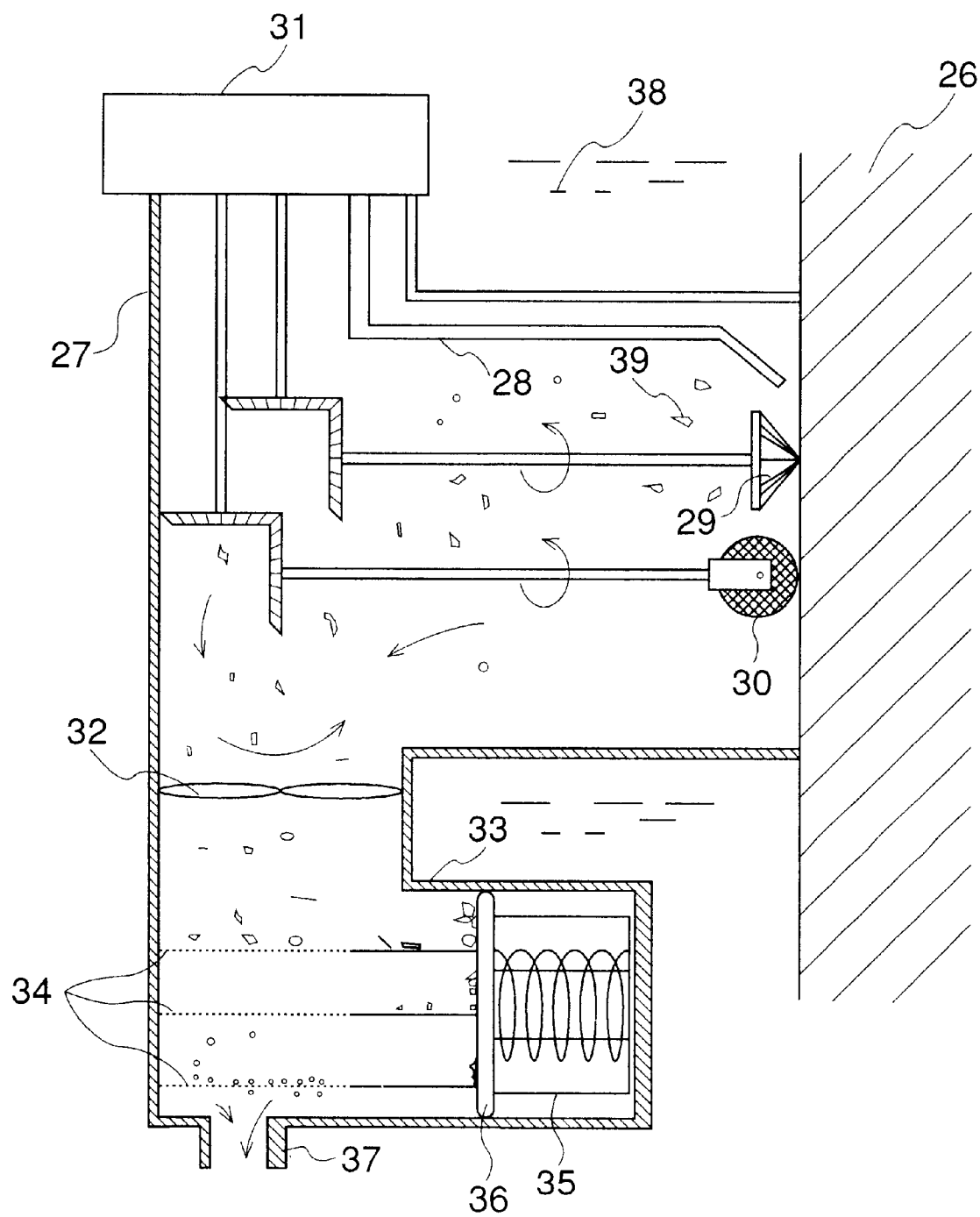
FIG. 13 is a schematic sectional view showing a method of sampling a structural material from the BWR plant.
Figure 14:
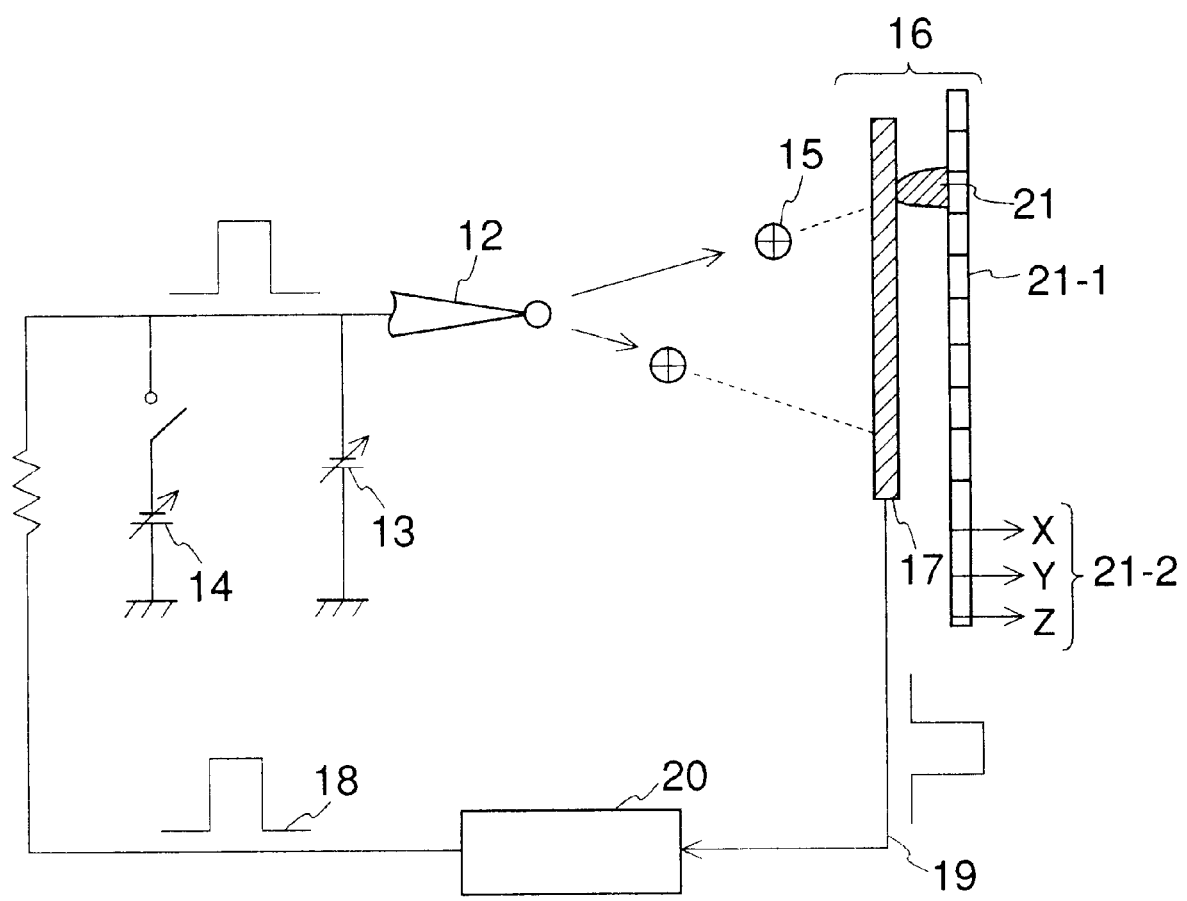
FIG. 14 is a schematic diagram showing the outlines of a 3-dimensional atom probe device.

Next, the method of taking a sample out of the foregoing actual plant will be described with reference to FIG. 13.

In this embodiment, a sampling method stated in Japanese Patent Application Laid-open No. 78747/1990 was employed. The sampling method is such that, as shown in FIG. 13, while a location to be sampled is being confirmed through a fiberscope 28, the wall 26 of the structural material is scraped by a drill 29 which is rotated by a driving device 31. The cut debris (as the sample) 39 of the structural material are collected by water currents which are created by a water-jet pump 32. Herein, the cut debris 39 are attracted onto a sampling plate 36 by an electromagnet 35. In this case, the cut debris 39 are assorted in accordance with predetermined sizes by filters 34.

The aforementioned parts of a sampling system are housed in a sampling vessel 27. Besides, owing to the presence of the filters 34, the cut debris (as the sample) 39 of the structural material are prevented from flowing out of the sampling system. In FIG. 13, numeral 30 designates an abrasive, numeral 33 a floating mineral dressing portion, numeral 37 an exhaust port, and numeral 38 a cooling water region in the plant.

Next, a practicable method for acquiring information on the inhomogeneity of the material will be described. In this embodiment, the information was obtained in such a way that the sample taken out by the system shown in FIG. 13 was analyzed using a 3-dimensional atom probe. The 3-dimensional atom probe will be outlined with reference to FIG. 14 below.

The sample 12 taken out of the plant is introduced into the analysis chamber (held in a vacuum at a level of $10^{-10}$ (Torr)) of the 3-dimensional atom probe. A positive high voltage 13 of several kilovolts is gradually applied to the sample 12. Further, a pulse voltage 14 is superimposed on the applied voltage. Then, surface atoms at the tip of the needle-shaped sample 12 are evaporated by an electric field, and they fly as ions 15. Herein, the ions 15 having separated are sensed by a microchannel plate 17 which is included in a position detector 16. A timer 20 measures the flight time period of each ion 15 by utilizing a start signal 18 synchronized with the pulse voltage 14, and a stop signal 19 indicating the sensing of the ion by the microchannel plate 17. Since the flight time period of the ion 15 is proportional to the mass thereof, the species of the evaporated ion is known from the measured result of the flight time period.

Further, an electron cloud 21 generated within the microchannel plate 17 by the arrival of the ion 15 enters a wedge strip type anode 21-1 located behind this plate 17. The electron cloud 21 is divided among three electrodes included in the wedge strip type anode 21-1, and the resulting charge signals 21-2 are transferred to a computer. The position of the ion 15 which has flown across flying can be calculated from the ratio of charges divided among the three electrodes. The data of the species and positions of the ions 15 numbering several hundred thousand per sample are accepted, and the depth of an analytical region is presumed on the basis of the applied voltage of the sample and the crystal structure thereof. Thus, the distribution of the atoms having originally existed at the tip of the sample can be stereoscopically reconstructed by the use of the image processing computer.

Figure 15:
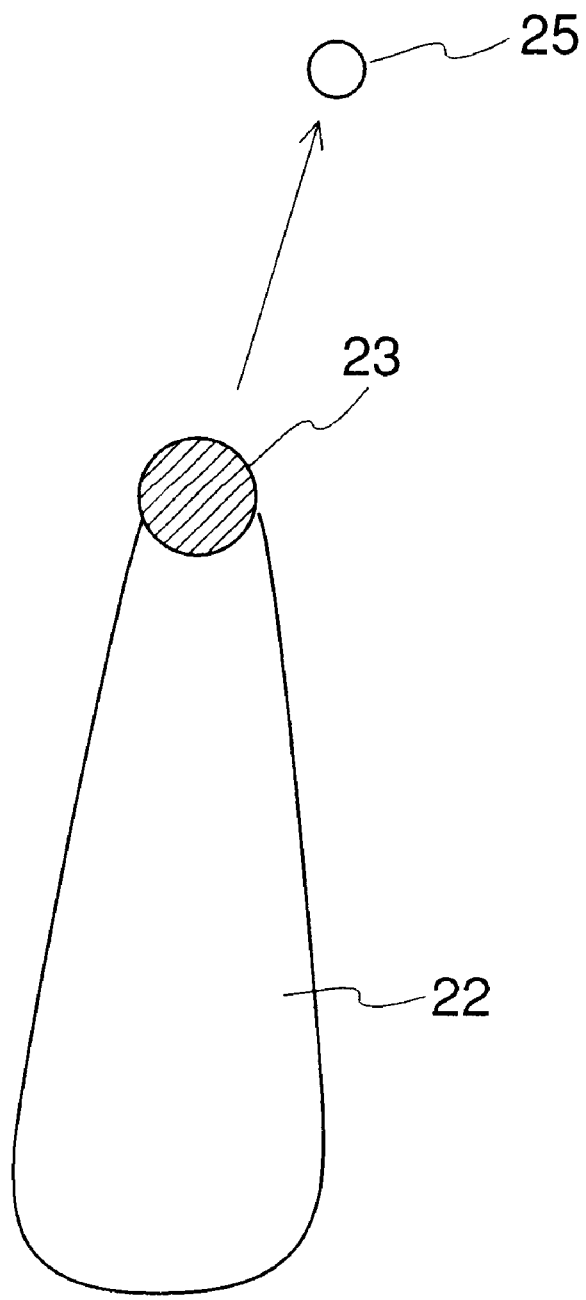
FIG. 15 is a schematic view showing the situation of the tip of a needle-shaped sample.
Figure 16:
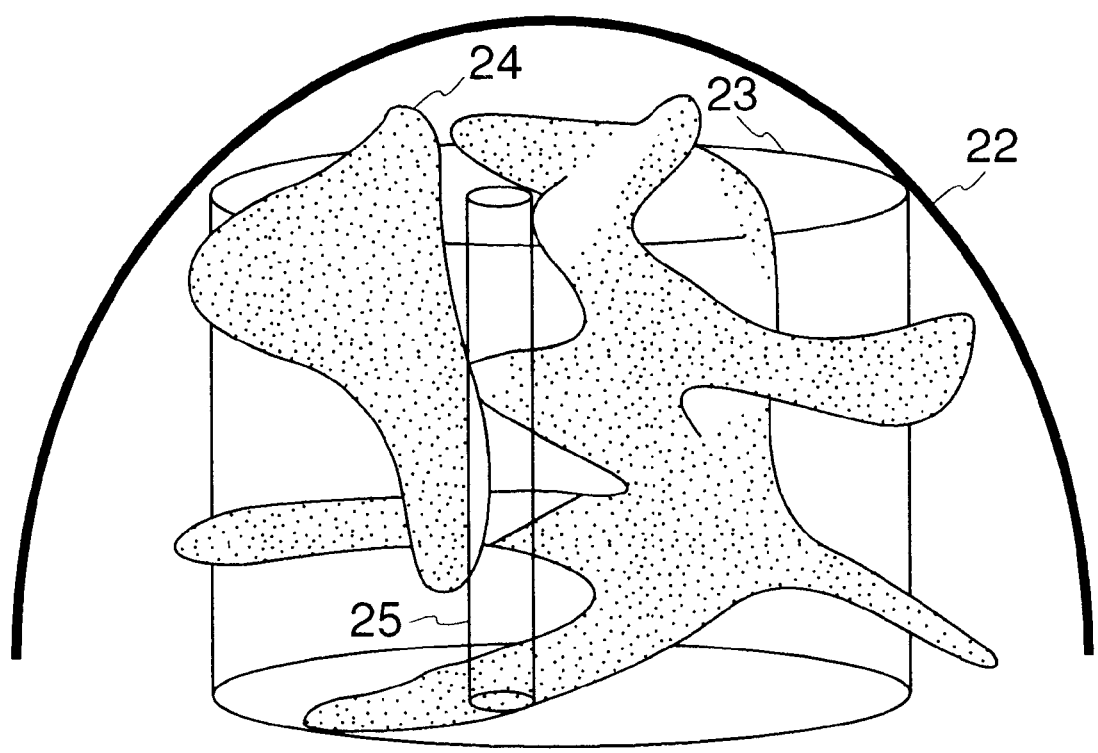
FIG. 16 is an enlarged view showing the details of an analytical region at the sample tip.

FIG. 15 is an enlarged view of the tip of the needle-shaped sample. Numeral 22 designates the sample, numeral 23 the analytical region, and numeral 25 a noticed analytical subregion (selected subregion). In a case where an actual plant material which has drastically deteriorated has been sampled, a high chromium phase 24 and a low chromium phase which have a 3-dimensional stitch structure are stereoscopically observed in the columnar analytical region 23 at the tip of the sample 22 as shown in FIG. 16.

Embodiment 2

Figure 17:
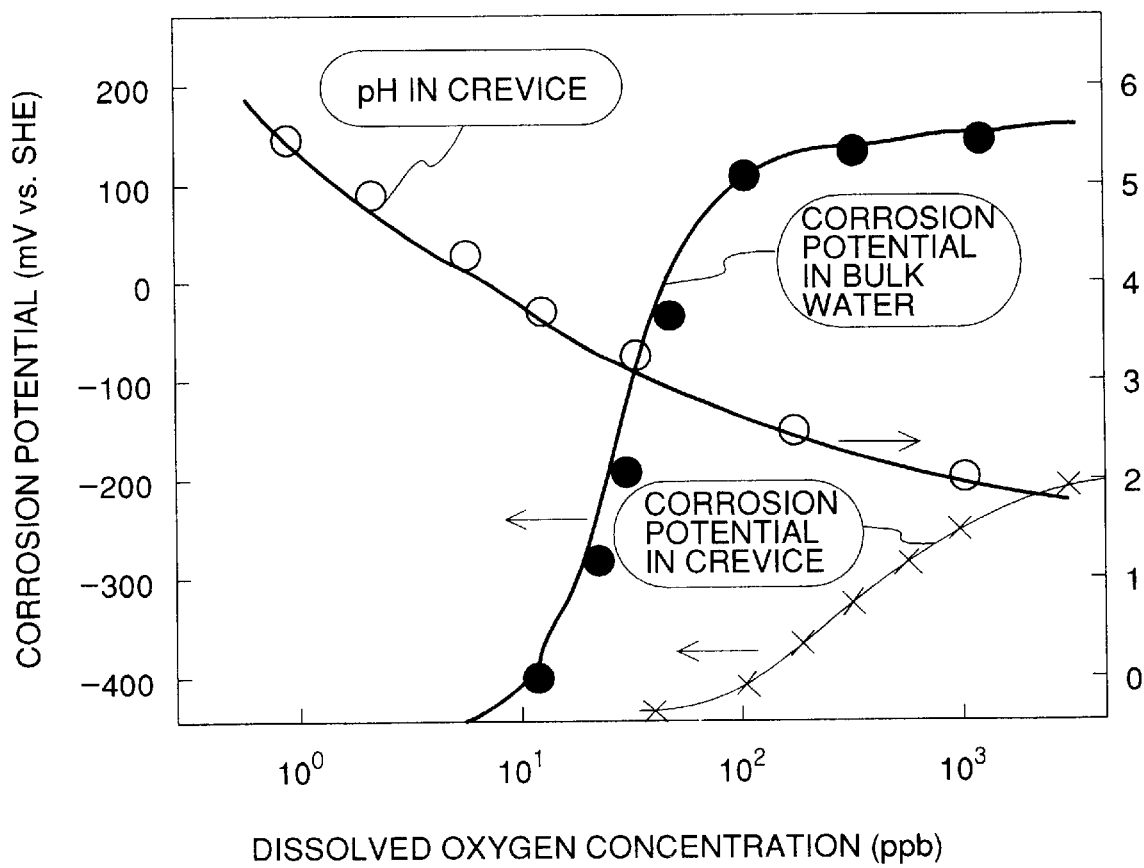
FIG. 17 is a graph showing the relationships between respective corrosion potentials in a crevice and bulk water and the concentration of oxygen dissolved in the bulk water, and the relationship between pH in the crevice and the dissolved oxygen concentration.

FIG. 17 illustrates the relationships between the concentration of dissolved oxygen and corrosion potentials in a crevice and in bulk water. Also, it illustrates the relationship between the dissolved oxygen concentration and pH in the crevice. Data indicated in the figure were obtained in such a way that a test piece of stainless steel was formed with a gap simulative of a microcrevice, and that the test piece was immersed in the environment of pressurized and elevated-temperature water, whereupon the concentration of oxygen in the pressurized and elevated-temperature water was changed. The data were measured by inserting a pH sensor and a corrosion potential sensor into the gap. The difference between the corrosion potentials in the crevice and in the bulk water as shown in FIG. 17 corresponds to the "potential difference between the corrosive environment and the interior of a microcrevice" mentioned in the appended claims.

The corrosion potential of the stainless steel was about 150 (mV vs. SHE) (a value measured by the system shown in FIG. 11) before hydrogen injection. This potential is high compared with the potential level (−160 (mV vs. SHE) obtained by the photoelectrochemical measurement) of the valence band of the passive film of the stainless steel whose grain boundary had its chromium content lowered by the thermal sensitization. It is accordingly anticipated from FIG. 17 that, in the oxidizing environment, the pH in the passive film of the test piece once broken down by a stress will lower to the level of 2.5. Besides, the corrosion potential of the tip of the crevice was about −300 (mV vs. SHE). Chromium and iron oxides which are stable at the tip of the crevice in the state in which the pH and corrosion potential of the crevice tip assume such values, are $FeCr_2O_4$ and $Fe_3O_4$ (D. Cublcclottl and L. Ljungberg: J. Electrochem. Soc., 132.987 (1985)).

The oxide $Fe_3O_4$ has an electric conduction form close to that of metal, and it cannot satisfactorily function as the passive film. That is, the state in which the oxide $Fe_3O_4$ is formed is quite equivalent to the state in which the passive film is absent. There is a very high possibility that elution at the crevice will be accelerated by the absence of the passive film (the formation of the oxide $Fe_3O_4$).

Assuming that the microcrevice has grown up to the level at which a stress intensity factor can be defined, a time period in which the material is destroyed can be conjectured as explained below. In a case where the material has undergone a stress of constant load not less than a value $K_{1SCC}$ indicated in FIG. 4, the crack propagation rate of the material in the severest set conditions is calculated on the basis of Andresen et al.'s estimation formula (P. L. Andresen and F. P. Ford: Materials Science and Engineering, A103, pp. 167–184 (1988)), so as to evaluate the propagation rate of cracking ascribable to the stress corrosion of the material in the pertinent material environment. Andresen and Ford have estimated the propagation rate da/dt of the cracking of the stainless steel under the constant load condition as attributed to SCC (stress corrosion cracking), in accordance with the following equation [1]:

$$da/dt = 7.8 \times 10^{-3} \times n^{3.6} (6 \times 10^{-14} K^4)^n (cm/s) \quad [1]$$

In Eq. 1, letter K denotes the stress intensity factor (the dimensions thereof in Eq. 1 are ksi√in (kilo pound square inches √inch)=3.54 kg/(mm)$^{1.5}$=1 MPa√m). n is given as a function of the corrosion potential in a water chemistry condition to which the material is subject, the thermal sensitization level (EPR) of the material and the electric conductivity of the cooling water. In the system shown in FIG. 11, the corrosion potential at the pressure vessel bottom under the ordinary water chemistry condition without the hydrogen injection is about −150 (mV vs. SHE), and the conductivity of the water is at the level of 0.1 ($\mu$S/cm). Here, it is assumed for predictive maintenance that the conditions of the material are the worst. That is, EPR=30 Ccm$^{-2}$ is assumed as the sensitization level of the material, and the stress intensity factor=31 MPa√m as the stress of the pertinent part. Andresen and Ford have given n≈0.6 as the value of the function a under the above environmental conditions.

Thus, the crack propagation rate da/dt is calculated to be da/dt≈0.2 (cm/year). On the other hand, in a case where the corrosion potential has been lowered to the level of −200 (mV) by the hydrogen injection shown in FIG. 12, the SCC propagation rate of the material decreases to 0.02 (cm/year). As understood from the above description, when the hydrogen injection is carried out, the oxidizing power of the cooling water environment can be lowered to render the corrosion potential below the valence band potential level (−160 (mV vs. SHE) of the thermally sensitized material. In this way, a process from the growth of a microcrevice to the propagation of the SCC can be hindered. Further, it is possible to sharply lower the propagation rate of that crack of the material which has already appeared before the hydrogen injection. It is accordingly indicated that the method of lowering the corrosion potential on the basis of the hydrogen injection in FIG. 12 is appropriate also in point of ensuring the re-passivation of the passive film after the breakdown thereof and suppressing the process from the microcrevice growth to the SCC propagation.

Embodiment 3

This embodiment concerns a technique in which the valence band level EV of an oxide film formed at the surface of a structural material is theoretically determined by a molecular orbital method, whereupon an alloy is designed so as to have the optimum composition conforming to desired service conditions.

Figure 18:
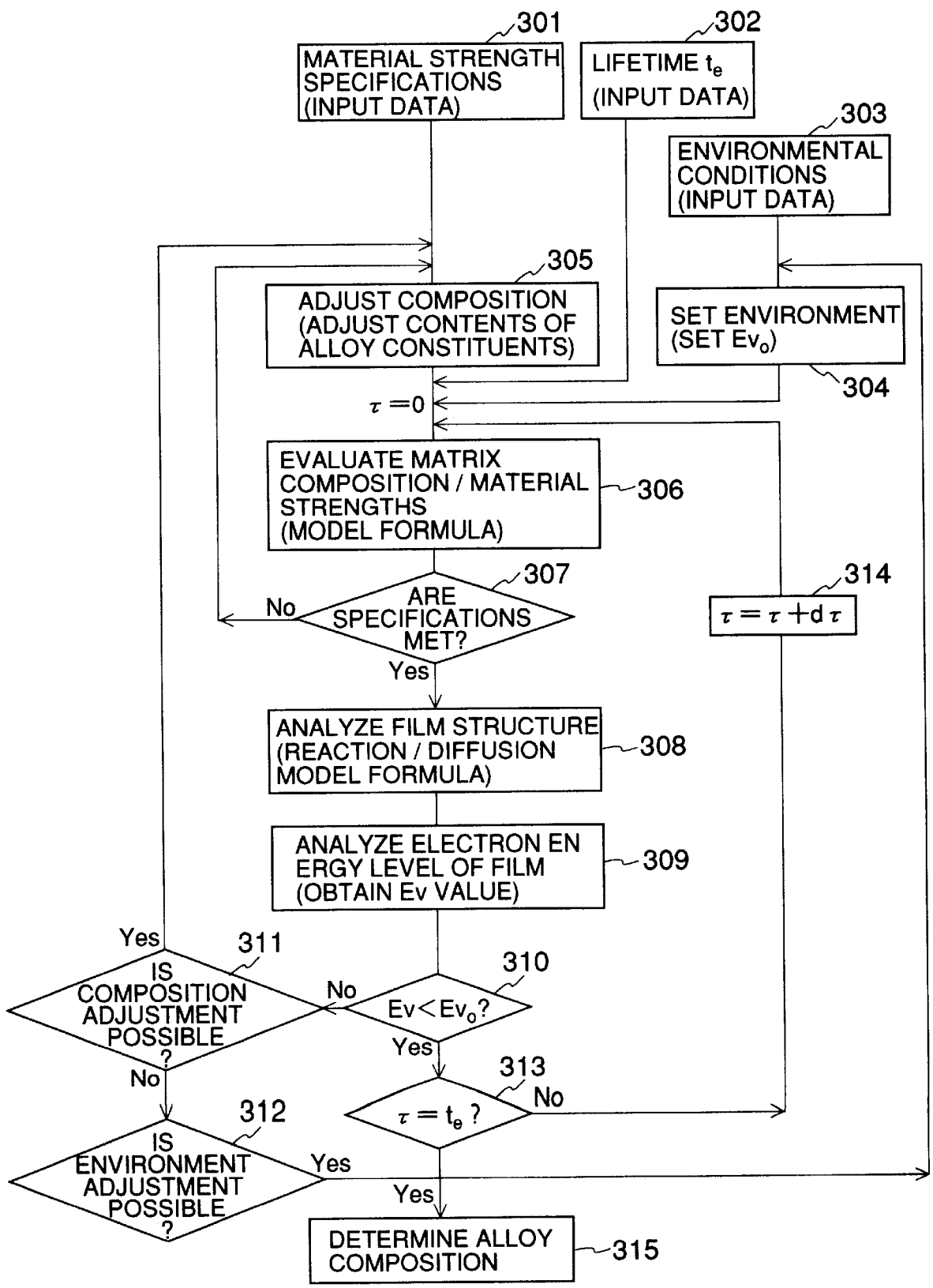
FIG. 18 is a flow chart showing processing steps in the third embodiment of the present invention.

Steps in the alloy designing method of this embodiment are illustrated in FIG. 18.

First, material strength specifications, service environment conditions and a service lifetime are set in correspondence with the service conditions (steps 301, 302 and 303). The yield strength, stiffness and tensile strength of the alloy, for example, are mentioned as the material strength specifications. The pH, temperature, electric conductivity and solute concentrations of reactor cooling water, for example, are mentioned as the service environment conditions.

Subsequently, the maximum allowable value $Ev_o$ of the valence band level Ev corresponding to the environmental conditions is set by utilizing the relationship among the corrosion potential, Fermi level and valence band level of the alloy (step 304). Data separately obtained beforehand are used as the corrosion potential, Fermi level and valence band level which are required here.

Further, the composition of the alloy is adjusted (step 305), and whether or not the composition satisfies the material strength specifications is checked using evaluation models for material strengths (steps 306 and 307). Unless the material strength specifications are satisfied, the flow of the alloy designing method returns to the step 305, at which the alloy composition is adjusted. The adjustment and evaluation of the alloy composition are iterated until the composition satisfying the set material strength specifications is obtained. Secular change effects, such as thermal aging and irradiation embrittlement, shall also be included in the material strength evaluation. In a case where the composition satisfying the material strength specifications has been obtained, the flow proceeds to a step 308.

The step 308 functions to find the structure of an oxide film to be formed on the surface of the matrix of the composition which has been determined at the steps 305–307 under the input environmental conditions of the step 303. The structure of the oxide film is obtained by evaluating the diffusion/corrosion behaviors of the matrix with model formulas.

Figure 19:
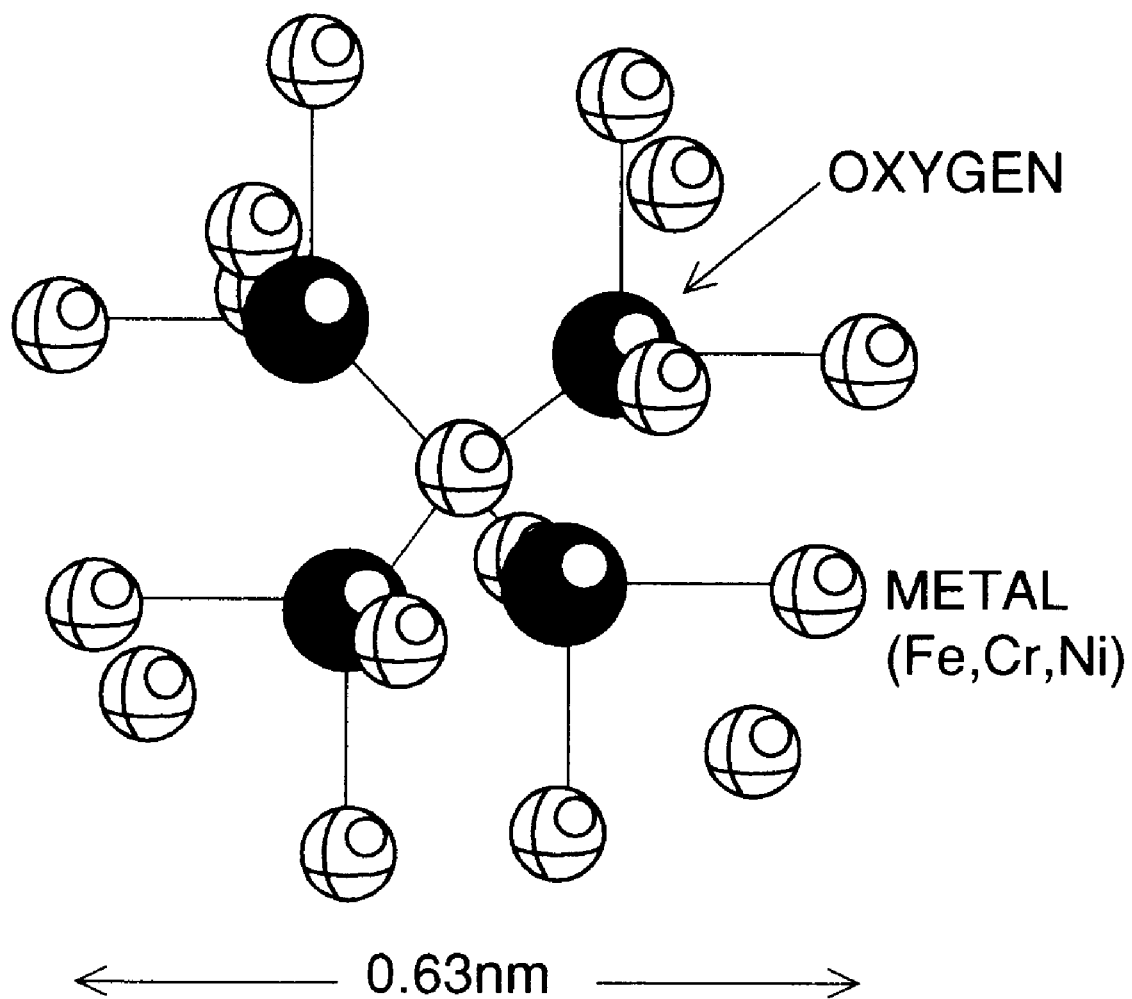
FIG. 19 is a model diagram showing the minimum recurrence structure of the oxide of an Fe—Ni—Cr alloy.

Further, as to the oxide film structure obtained, the valence band level Ev for the bulk structure is calculated by the molecular orbital method (step 309). As shown in FIG. 19, a calculation cluster is set at a size which is not smaller than the minimum recurrence structure. In the figure, stainless steel which is utilized as the structural materials of various plants is referred to, and one example of the oxide film thereof in the elevated-temperature water is illustrated. As to the calculation cluster, a wave function φ which satisfies the following equation [2] is calculated by the molecular orbital method:

$$H\phi = E\phi \qquad [2]$$

$H$: Hamiltonian $E$: Energy eigenvalue

Figure 20:
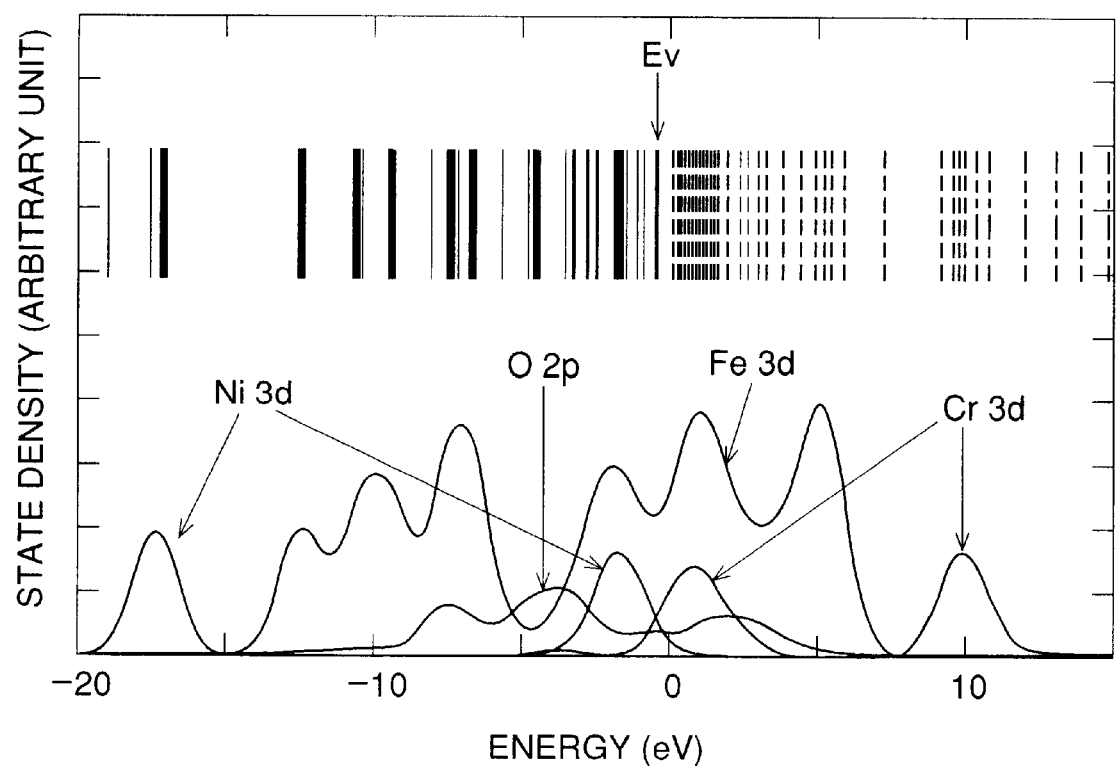
FIG. 20 is a graph showing the energy levels of electrons in atoms which constitute a calculation cluster.
Figure 21:
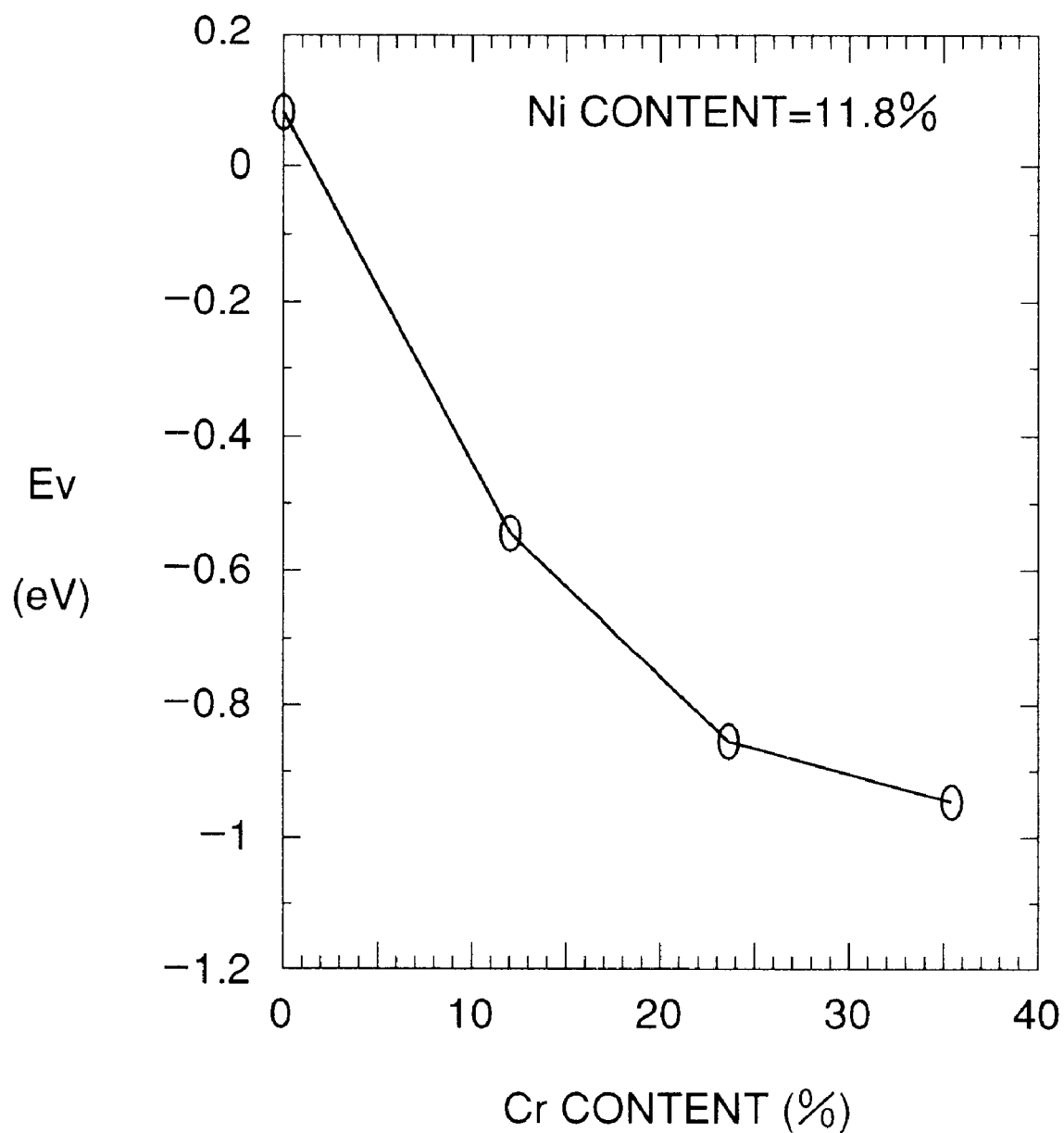
FIG. 21 is a graph showing the relationship between the Cr content of an oxide film of spinel structure and the energy levels of the electrons thereof, the oxide film containing Cr and Ni besides a principal component $Fe_3O_4$.

Although there are various molecular orbital methods, a density functional theory or method with which a solution of high accuracy is obtained "a priori" is one well-suited method. With this method, energy levels can be calculated for the electrons of respective atoms constituting the calculation cluster, as illustrated in FIG. 20, and the valence band level Ev can be determined from the energy levels. FIG. 21 illustrates an example of evaluation of the oxide film of spinel structure containing $Cr_3Ni$ besides a principal component $Fe_3O_4$. The illustrated example indicates the tendency that, as the Cr content in the film decreases, the valence band level Ev of the metal rises to degrade the corrosion resistance thereof.

Referring back to FIG. 18, the magnitudes of the valence band level Ev thus obtained and the maximum allowable value $Ev_o$ set from the environmental conditions are compared (step 310). In a case where $Ev > Ev_o$ holds as the result of the comparison, the flow returns to the step 305 in order to iterate the series of steps again by first altering the alloy composition, and similar processing is iterated (step 311). In a case where the requisite of the step 310 cannot be met merely by adjusting the composition within a range adapted for the material strength specifications, the flow returns to the step 304 in order to adjust the service environment conditions within a possible range, and similar processing is iterated (step 312).

In a case where $Ev < Ev_o$ holds at the step 310, the alloy having the pertinent composition satisfies both the material strength specifications and the environment specifications, at least, at the start of service or use (t=0). Therefore, whether or not the above evaluations will hold-true throughout the expected lifetime ($t_e$) of the material is lastly checked (steps 313 and 314). The check is performed in such a way that, while τ is being increased every dτ, the evaluations of the steps 306 thru 310 are confirmed anew. In a case where any of the various specifications will not be met midway of the expected lifetime as the result of the check, the composition and the service environment conditions are adjusted, and the processing is redone from the beginning (from the step 305).

In a case where $τ=t_e$ holds at the step 313, the composition on that occasion is an alloy composition which satisfies all the required specifications (step 315).

In a case where the environment adjustment is 10 impossible at the step 312, the alloy satisfying the required specifications can no longer be prepared. Accordingly, the specifications themselves are studied again.

In the above, the model formulas are utilized concerning the formation of the oxide film structure at the step 308. It is also possible, however, to apply the molecular orbital method instead of the model formulas. More specifically, since the potentials of the diffusion and reaction of atoms can be determined by the molecular orbital method, the oxide film formation based on the corrosion reaction and diffusion can be theoretically simulated by molecular dynamics. Likewise, in the evaluation of the material strengths at the step 306, the formation, diffusion and growth behavior of a point defect may well be analyzed using the potential energy of the atomic diffusion calculated by the molecular orbital method. Thus, the alloy composition-dependency of the material strengths can be evaluated without resorting to the empirical model formulas. This technique is effective for analyzing the irradiation embrittlement in a neutron irradiation environment as in the interior of a nuclear reactor, or for analyzing the irradiation effects of a material, such as irradiation-induced segregation, irradiation creep and irradiation-induced stress relaxation.

As described above, according to this embodiment, the electron energy level of the oxide film is calculated by the molecular orbital method. Thus, the energy level is theoretically evaluated at high precision without resorting to the empirical formulas or experimental laws, whereupon the optimum alloy composition conforming to the service condition specifications of the material strengths and the environment can be determined. Since no empirical formula is used, the technique of this embodiment is, in principle, applicable to a wide range of alloy compositions. Even in a case where the sort of steel or the environment of the plant differs, an evaluation formula need not be added by a new experiment or the like, and an evaluation at the same high precision is possible.

In setting the maximum allowable value $Ev_o$ at the step 304, the inhomogeneous composition of the oxide film should also preferably be taken into consideration. The degree of the inhomogeneity can be detected using any of various surface analysis apparatuses which have hitherto been known. The relationship between the composition and the valence band level is calculated by the molecular orbital method or the like beforehand. The discrepant range of the valence band level at the surface of the film, etc. can be obtained by comparing the detected result and the calculated result.

Embodiment 4

This embodiment concerns a plant operation controlling method and a plant operating system which are intended to enhance a corrosion resistance or to prevent/suppress a corrosion resistance from lowering, by utilizing the evaluated result of a valence band level Ev based on a molecular orbital method.

Figure 22:
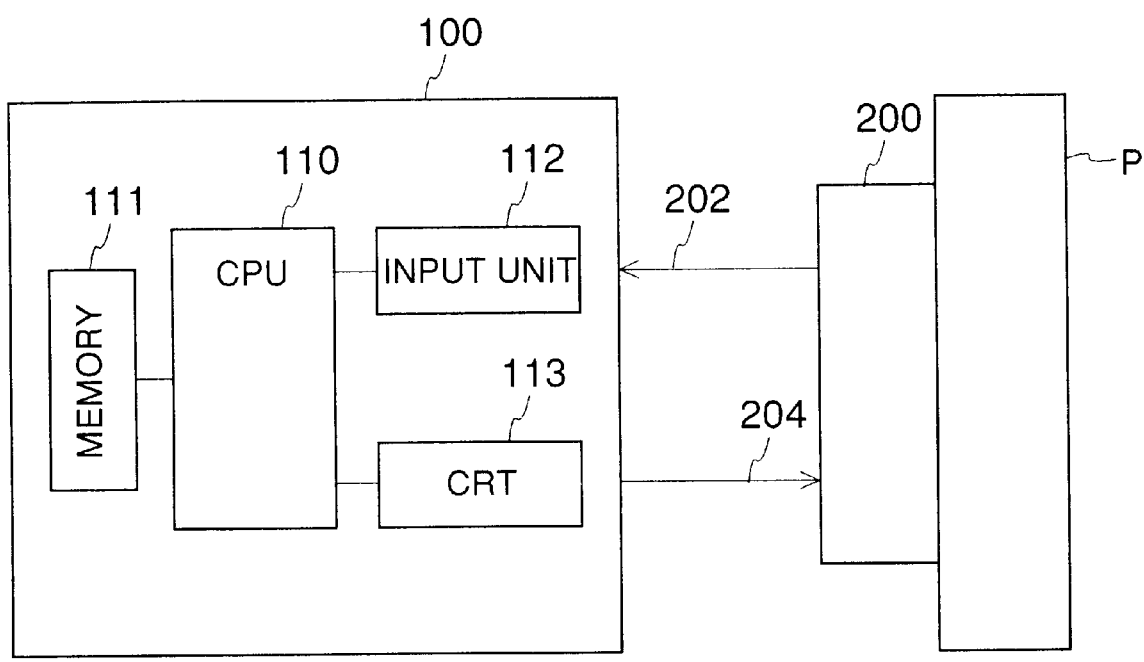
FIG. 22 is a block diagram showing the outlines of a plant operating system in the fourth embodiment of the present invention.

The outlines of the plant operating system are illustrated in FIG. 22.

The plant operating system is constructed including a data analysis device 100 and an environment control device 200. In the figure, letter P denotes a plant which is to be controlled.

The environment control device 200 serves to detect information indicative of an environmental state in the plant P (hereinbelow, called the "plant environment information"), and to control the environmental state. A temperature, pH, electrical conductivity, etc. are mentioned as the items of the plant environment information. Accordingly, the environment control device 200 includes a temperature sensor, pH sensor, electrical conductivity sensor, etc. However, it need not include all the sensors, but may include only the sensors which are required for controlling the internal environment of the plant P to-be-controlled. In a case where the sensors are included in the plant P itself, they may well be diverted. The environment control device 200 delivers the detected plant environment information 202 to the data analysis device 100.

Further, the environment control device 200 includes means for controlling the environment in the plant P. This embodiment is so constructed that the pH in the plant P can be controlled by injecting an alkali. The control of the internal environment of the plant P is performed in accordance with the controlled variable 204 of the plant P supplied from the data analysis device 100.

The data analysis device 100 serves to evaluate the internal environment of the plant P, and to determine a desired environmental condition in the environment control of the environment control device 200. This data analysis device 100 is endowed with, for example, the function of evaluating the valence band level Ev which is the most important in the present invention, by the use of the data received from the environment control device 200, etc. The molecular orbital method itself is not handled in the data analysis device 100, but model formulas are obtained beforehand on the basis of results which have been previously computed for a computation system corresponding to the plant environment as a controlled system. A calibration formula for a plant monitor output value shall also be included in the model formulas.

Figure 23:
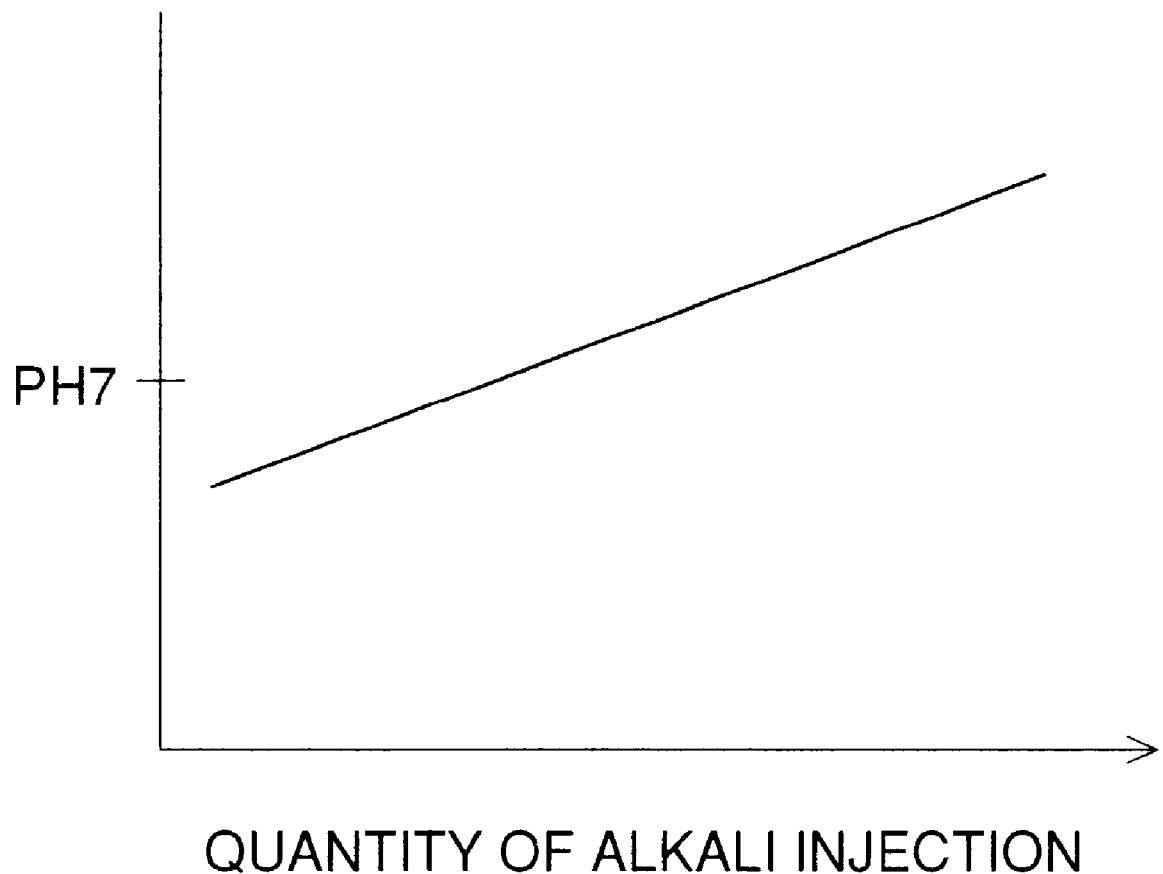
FIG. 23 is a graph showing an example of information which indicates the corresponding relationship between the controlled variable of a plant and the internal environment of the plant.

In addition, the data analysis device 100 is previously endowed with information which indicates the corresponding relationship between the controlled plant variable 204 to be delivered to the environment control device 200 and the environmental condition in the plant P. By way of example, in this embodiment, the device 100 has the corresponding relationship between the quantity of alkali injection into the plant P and the pH of cooling water in the plant P as shown in FIG. 23. Incidentally, such information is separately obtained beforehand. The data analysis device 100 determines the controlled plant variable for realizing the required environmental condition, by reference to the information. As already stated, the data analysis device 100 delivers the controlled plant variable (signal 204) to the environment control device 200. Besides, the data analysis device 100 has the function of calculating an elapsed term since the start of the operation of the plant P, and so forth.

The data analysis device 100 in a practicable form is constructed including a processor 110, a memory device 111, an input unit 112 and a display unit 113. The functions mentioned above are implemented in such a way that the processor 110 executes programs stored in the memory device 111. The aforementioned information (in FIG. 23) which indicates the corresponding relationship between the controlled plant variable and the internal environmental condition of the plant P, is also stored in the memory device 111.

Figure 24:
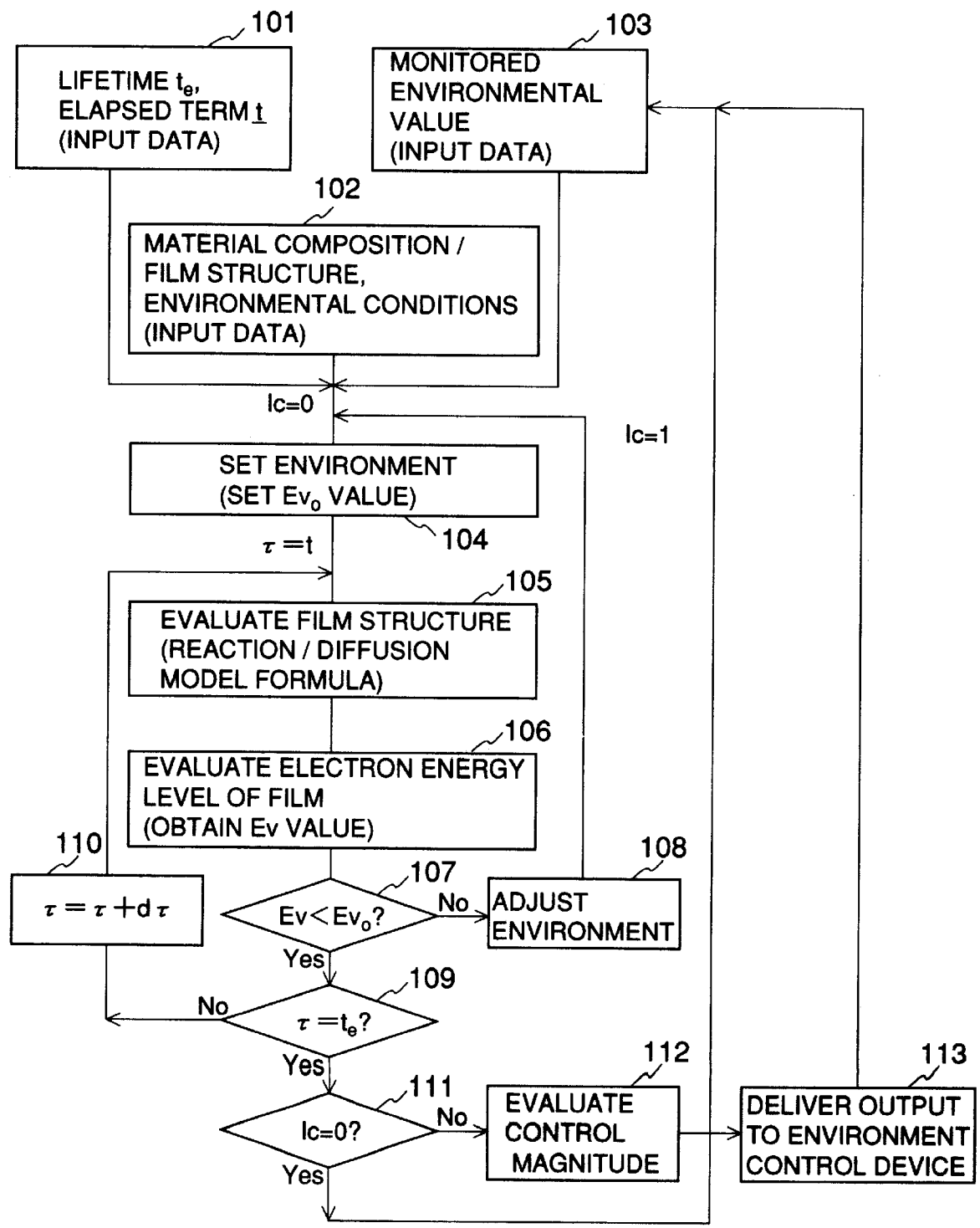
FIG. 24 is a flow chart showing processing which proceeds in a data analysis device.

Next, processing which the data analysis device 100 executes in the operation control of this embodiment will be described with reference to a flow chart illustrated in FIG. 24.

The data analysis device 100 is supplied as input data with the alloy composition and passive film structure of a plant structural material, the controllable range (environmental condition) of the service environment, the lifetime ($t_e$), and the elapsed term ($t$) since the start of use, by the supervisor of the plant P (steps 101 and 102). These data are not altered in view of the natures thereof. Accordingly, when the input values at the start of the plant operation are saved, the above data need not be entered thenceforth each time the processing shown in FIG. 24 is executed.

Besides, the data analysis device 100 is sequentially supplied with the signals 202 which correspond to the plant environment information (monitored environmental value) indicative of the actual internal environment of the plant P on each occasion, from the environment control device 200 (step 103).

Subsequently, the data analysis device 100 sets the maximum allowable value $Ev_o$ corresponding to the input environmental condition, on the basis of the above input data (step 104). Also, the structure of the surface oxide film corresponding to the environmental condition is found as a secular change in accordance with the model formulas of corrosion reaction/diffusion equations in the same manner as in the preceding embodiment (step 105).

Further, the electron energy level Ev of the oxide film structure at the set time (here, the elapsed term since the start of the plant operation) $t$ is calculated by the molecular orbital method as in the preceding embodiment (step 106). The calculated level Ev is compared with the value $Ev_o$ (step 107). If $Ev_o<Ev$ holds, the environment is currently liable to corrode the oxide film of the structural material. Therefore, conditions applied to the processing of the step 104, etc. are appropriately altered in order to attain an environmental condition which can suppress the proceeding of the corrosion (step 108). On this occasion, a flag $1c$ is raised (set to "1"). Next, the flow of the operation control returns to the step 104, at and after which the new environmental condition set at the step 108 is submitted to the evaluation of the electron energy level of the oxide film by the same processing as in the last cycle.

The processing of the steps 104 thru 108 is iterated until the requirement of $Ev_o>Ev$ holds.

In the case where $Ev_o>Ev$ holds at the step 107, the environmental condition on that occasion is an appropriate one which can ensure the corrosion resistance of the oxide film. Thus, the environmental condition which is necessary for suppressing the corrosion, at least, on that occasion has been obtained in calculation.

Thereafter, whether or not the satisfactory corrosion resistance will be maintainable throughout the expected lifetime ($t_e$) under the pertinent environmental condition is further checked. The check is performed in such a way that, while $\tau$ is being increased every $d\tau$ from $t$ to $t_e$ (step 110), the processing of the steps 105 thru 107 is iterated (step 109). In a case where the requirement of the step 107 will not be met midway of the expected lifetime $t_e$ as the result of the check (that is, in a case where the maintenance of the satisfactory corrosion resistance throughout the lifetime $t_e$ has been found to be impossible), the conditions are altered, and the processing is redone from the beginning (from the step 104).

In a case where $\tau=t_e$ holds at the step 109, the satisfactory corrosion resistance will be maintained throughout the lifetime $t_e$ under the pertinent environmental condition. This time, the data analysis device 100 controls the environment control device 200 so that the actual internal environment of the plant P may conform to the pertinent environmental condition. In this case, whether or not the calculated environmental condition (refer to the steps 104 thru 108) differs from the current environmental condition can be judged by reference to the flag $1c$ (step 111). In a case where $1c=0$ is held, that is, in a case where the satisfactory corrosion resistance has been ensured under the actual environmental condition itself entered from the environment control device 200, this device 200 need not be operated anew. Accordingly, the processing is ended without any further step.

On the other hand, in the case where $1c=0$ is not held, the data analysis device 100 determines the magnitude of the controlled plant variable (step 112), and it delivers the determined control magnitude to the environment control device 200 (step 113). The magnitude of the controlled plant variable is calculated using the relationship between the environmental condition and the controlled plant variable (refer to FIG. 23) as has been prepared in the data analysis device 100 beforehand. The environment control device 200 controls the internal environment of the plant P in compliance with the command of the data analysis device 100. In this embodiment, the device 200 injects the alkali in compliance with the command.

Also in this embodiment, the control precision can be heightened more by utilizing the molecular orbital method and the molecular dynamics for the evaluation of the oxide film structure in the same manner as in the preceding embodiment. As in the analysis of the electronic structure of the oxide film, however, it is appropriate for a quick plant control that the throughput of the plant operating system is relieved by preparing the model formulas with the previously calculated results.

In some ranges in which the plant environments are adjustable, the requirement of $Ev_o>Ev$ cannot be held throughout the expected lifetime. Even in such a case, the remaining lifetime of the material can be evaluated by evaluating a term for which the requirement can be satisfied.

As described above, according to this embodiment, the electron energy level of the oxide film is theoretically derived by the molecular orbital method, whereupon the controlled plant variable is calculated, so that the plant control with the corrosion resistance ensured is permitted without resorting to the empirical formulas or experimental laws. Further, when this embodiment is applied to the evaluation of the remaining lifetime of the material, an appropriate plan for predictive maintenance can be formed.

In the foregoing embodiments, only the electron level (Ev) of the valence band has been chiefly noted. However, when the conductivity type of the semiconductor forming the oxide film, the width of the band gap, and the inhomogeneity of the material composition are also considered, an alloy design, a plant operation, etc. which are more precise can be realized.

Incidentally, when the known electrochemical techniques and the techniques according to the present invention are applied in combination, a corroded state can be evaluated more precisely.

The present invention achieves effects as stated below.

According to the present invention, an environment in a plant (for example, a cooling water chemistry in a nuclear power plant) can be controlled so as to bring a structural material into a stable condition. Besides, an alloy of high corrosion resistance can be designed on the basis of a theoretical background. When the semiconducting characteristics etc. of a sample are compared with those of a reference material, the soundness etc. of the sample can be evaluated.

When the corrosional damage evaluating method of the present invention is combined with the corrosional damage evaluating method based on the electrochemical technique or the like in the prior art, the studied results of corrosional damages in the prior art can be evaluated at a higher precision. A film deterioration breakdown for the initiation of SCC can be theoretically handled.

What is claimed is:

1. A method of designing an alloy of high corrosion resistance for a metal material which is corroded upon contact with a corrosive environment; comprising the steps of:

diagnosing either of a microcracking property and passive film breakdown characteristics of the metal material from a relationship between:

at least one item of information from among a chemical composition of said metal material, information on a passive film to be formed on said metal material, and information on a corrosion potential of said metal material in the corrosive environment; and either of information items on a microcrack of said metal material and breakdown of the passive film of said metal material in said corrosive environment; and determining the chemical composition of said metal material on the basis of either of the diagnosed microcracking property and passive film breakdown characteristics.

2. A method of designing an alloy of high corrosion resistance for a metal material which is exposed to a corrosive environment, comprising the steps of:

diagnosing a stress corrosion cracking property of the metal material in the corrosive environment from a relationship between:

at least one item of information from among a condition for elution of said metal material, a condition for appearance of a microcrevice in said metal material, a change of pH within the microcrevice, a condition for incapability of generating a passive film within said microcrevice, a potential difference between the corrosive environment and the interior of said microcrevice, and a condition for growth of said microcrevice, these information items being taken in said corrosive environment; and stress corrosion cracking characteristics of said metal material in said corrosive environment; and determining a chemical composition of said metal material on the basis of the diagnosed result.

3. A method of designing an alloy of high corrosion resistance for a metal material, comprising:

a first step of finding information on a corrosive environment of the metal material, and information on a corrosion potential of said metal material in the corrosive environment;

a second step of finding at least one item of information from among inhomogeneity in a chemical composition of said metal material, inhomogeneity in a passive film to be formed on said metal material, and inhomogeneities in compositions of said metal material at a grain boundary and within a grand boundary;

a third step of finding an energy level of electrons in a corrosion system on the basis of the corrosion potential, the corrosion system including the passive film and said corrosive environment; and a fourth step of determining a composition of the alloy on the basis of the electron energy level of said corrosion system as obtained in said third step, so that a corrosion potential range previously set for a service environment condition of said metal material and a Fermi level range of the electrons lies between a conduction band and a valence band of electrons in a semiconductor electronic structure of said passive film or oxide film of said metal material.

4. A method for designing an alloy of high corrosion resistance wherein the alloy is formed with a passive film on its surface, the passive film being a semiconductor, comprising the step of determining a composition of said alloy in accordance with: (a) within a predetermined range of change in an environment in which said alloy is to be placed, lowering a valance band level of said passive film to a level lower than a Fermi level of a corrosion system including said alloy and said environment; and (b) causing said passive film to become an n-type semiconductor.

* * * * *